US006991785B2

(12) United States Patent
Frey, II

(10) Patent No.: US 6,991,785 B2
(45) Date of Patent: Jan. 31, 2006

(54) METHOD FOR ADMINISTERING A CYTOKINE TO THE CENTRAL NERVOUS SYSTEM AND THE LYMPHATIC SYSTEM

(75) Inventor: William H. Frey, II, North Oaks, MN (US)

(73) Assignee: Chiron Corporation, Emeryville, CA (US)

( * ) Notice: Subject to any disclaimer, the term of this patent is extended or adjusted under 35 U.S.C. 154(b) by 201 days.

(21) Appl. No.: 10/102,163

(22) Filed: Mar. 20, 2002

(65) Prior Publication Data

US 2002/0141971 A1    Oct. 3, 2002

Related U.S. Application Data

(63) Continuation of application No. 09/733,168, filed on Dec. 8, 2000.

(60) Provisional application No. 60/200,708, filed on Dec. 9, 1999.

(51) Int. Cl.
*A61K 38/21* (2006.01)
*A61K 45/00* (2006.01)
*A61K 38/00* (2006.01)
*C07K 17/00* (2006.01)

(52) U.S. Cl. .................. 424/85.6; 424/85.7; 424/85.5; 424/85.4; 424/85.1; 514/2; 530/351; 530/350; 530/399

(58) Field of Classification Search ............... 424/85.6, 424/85.7, 85.5, 85.4, 85.1; 514/2; 530/351, 530/350, 399
See application file for complete search history.

(56) References Cited

U.S. PATENT DOCUMENTS

| | | | |
|---|---|---|---|
| 4,462,985 A | 7/1984 | Cummins | |
| 4,479,932 A | 10/1984 | Bodor | |
| 4,497,795 A | 2/1985 | Cummins | |
| 4,746,508 A | 5/1988 | Carey et al. | |
| 4,820,514 A | 4/1989 | Cummins | |
| 4,820,515 A | 4/1989 | Cummins | |
| 4,857,316 A | 8/1989 | Eppstein | |
| 5,017,371 A | 5/1991 | Cummins | |
| 5,019,382 A | 5/1991 | Cummins | |
| 5,145,677 A | 9/1992 | von Eichborn et al. | |
| 5,215,741 A | 6/1993 | Young et al. | |
| 5,482,706 A | 1/1996 | Igari et al. | |
| 5,514,670 A | 5/1996 | Friedman et al. | |
| 5,624,898 A | 4/1997 | Frey, II | |
| 5,676,942 A | 10/1997 | Testa et al. | |
| 5,817,307 A | 10/1998 | Cummins | |
| 5,824,300 A | 10/1998 | Cummins | |
| 5,830,456 A | 11/1998 | Cummins | |
| 5,846,526 A | 12/1998 | Cummins | |
| 5,853,763 A | 12/1998 | Tice et al. | |
| 5,882,640 A | 3/1999 | Cummins | |
| 5,910,304 A | 6/1999 | Cummins | |
| 6,036,949 A | 3/2000 | Richards et al. | |
| 6,048,843 A | 4/2000 | Tóth | |
| 6,060,450 A | 5/2000 | Soos et al. | |
| 6,127,332 A * | 10/2000 | Goelz et al. | |
| 6,361,769 B1 * | 3/2002 | Tovey ........................ 424/85.4 |
| 6,372,218 B1 | 4/2002 | Cummins | |

FOREIGN PATENT DOCUMENTS

| | | |
|---|---|---|
| EP | 0 504 263 B1 | 9/1992 |
| JP | 7041428 A | 2/1995 |
| SU | 1139444 A | 2/1985 |
| WO | WO 91/07947 A1 | 6/1991 |
| WO | WO 97/41884 A1 | 11/1997 |
| WO | WO 00/33814 A2 | 6/2000 |
| WO | WO 00/44350 | 8/2000 |
| WO | WO 00/44350 A1 | 8/2000 |

OTHER PUBLICATIONS

Sperber, S.J., et al. J. Infectious Diseases 1998, vol. 158(1), pp. 166-175.*
Sperber, S.J., et al. Archives of Otolarygology- Head and Neck Surgery 1992, vol. 118(9), pp. 933-936.*
Barbaro et al. (1999) "Intravenous Recombinant Interferon-Beta versus Interferon-Alpha-2b and Ribavirin in Combination for Short-Term Treatment of Chronic Hepatitis C Patients Not Responding to Interferon-Alpha," *Scand. J. Gastroenterol.* 34(9): 928-933.
Bocci et al. (1988) "The Lymphatic Route. V. Distribution of Human Natural Interferon-β in Rabbit Plasma and Lymph," *Journal of Interferon Research* 8(5): 633-640.
Chien et al. (1989) "Nasal Systemic Drug Delivery," *Modern Pharmaceutics* 39: 18-19, 44-49, 56-59, 82-85, 292-293.
Cui (2000) "A Plasmid Construct Encoding Murine Interferon Beta Antagonizes the Replication of Herpes Simplex Virus Type I In Vitro and In Vivo," *J. Neuroimmunology* 108:92-102.
Eppstein et al. (1988) "Alternative Delivery Systems for Peptides and Proteins as Drugs," *CRC Critical Reviews in Therapeutic Drug Carrier Systems* 5(2): 99-139.
Geiger (1997) "Interferon-γ Protects against Herpes Simplex Virus Type 1-Mediated Neuronal Death," *Virology* 238: 189-197.

(Continued)

*Primary Examiner*—Janet Andres
(74) *Attorney, Agent, or Firm*—Joel B. Silver; James Austin; Alisa A. Harbin

(57) ABSTRACT

The present invention is directed to a method for delivering cytokines to the central nervous system and the lymphatic system by way of a tissue innervated by the trigeminal nerve and/or olfactory nerve. Cytokines include tumor necrosis factors, interleukins, interferons, particularly interferon-β and its muteins such as IFN-$\beta_{ser17}$. Such a method of delivery can be useful in the treatment of central nervous system disorders, brain disorders, proliferative, viral, and/or autoimmune disorders such as Sjogren's disorder.

48 Claims, 1 Drawing Sheet

OTHER PUBLICATIONS

Gopinath et al. (1978) "Target Site of Intranasally Sprayed Substances and Their Transport Across the Nasal Mucosa: A New Insight into the Intranasal Route of Drug-Delivery," *Current Therapeutic Research* 23(5): 596-607.

Kakizaki et al. (1999) "Evaluation of Twice-Daily Administration of Interferon-β for Chronic Hepatitis C," *J. Viral Hepatitis* 6: 315-319.

Kida et al. (1993) "CSF Drains Directly from the Subarachnoid Space into Nasal Lymphatics in the Rat. Anatomy, Histology and Immunological Significance," *Neuropathology and Applied Neurobiology* 19: 480-488.

Lee et al. (1988) "Intranasal Delivery of Proteins and Peptides," *BioPharm.* pp. 30-37.

Leib et al. (1999) "Interferons Regulate the Phenotype of Wild-type and Mutant Herpes Simplex Viruses In Vivo," *J. Exp. Med.* 189: 663-672.

Minagawa et al. (1997) "Suppression of Infectious Virus Spread and Corneal Opacification by the Combined Use of Recombinant Interferon Beta and Interleukin-10 Following Corneal Infection with Herpes Simplex Virus-1 in Mice," *Antiviral Research* 36: 99-105.

Pelidou (2000) "Intranasal Administration of Recombinant Mouse Interleukin-12 Increases Inflammation and Demyelinaton in Chronic Experimental Autoimmune Neuritis in Lewis Rats," *Scand. J. Immunol.* 51: 25-35.

Peridou et al. (2000) "Enhancement of Acute Phase and Inhibition of Chronic Phase of Experimental Autoimmune Neuritis in Lewis Rats by Intranasal Administration of Recombinant Mouse Interleukin 17: Potential Immunoergulatory Role," *Experimental Neurology* 163: 165-172.

Ship et al. (1999) "Treatment of Primary Sjögren's Syndrome with Low-Dose Natural Human Interferon-α Administered by the Oral Mucosal Route: A Phase II Clinical Trial," *J. Interferon and Cytokine Res.* 19: 943-951.

Smith et al. (1987) "Intranasally Administered Alpha/Beta Interferon Prevents Extension of Mouse Hepatitis Virus, Strain JHM, into the Brains of BALB/cByJ Mice," *Antiviral Research* 8: 239-245.

Thorne et al. (date unknown) "Quantitative Assessment of Protein Transport to the Rat Olfactory Bulb Following Intranasal Administration: Implications for Drug Delivery," *Paper for Dept. of Neurology, St. Paul Ramsey Medical Ctr.* (20 pages).

Xiao et al. (1998) "Suppression of Acute and Protracted-Relapsing Experimental Allergic Encephalomyelitis by Nasal Administration of Low-Dose IL-10 in Rats," *J. Neuroimmuno.* 84: 230-237.

Thorne, R.G., "Delivery of Neurotrophic Factors to the Central Nervous System," *Clin. Pharmacokinet*, 2001, pp. 907-946, vol. 40(12).

Thorne, R.G., "Delivery of Insulin-Like Growth Factor-1 to the Brain and Spinal Cord Along Olfactory and Trigeminal Pathways Following Intranasal Administration: A Noninvasive Method for Bypassing the Blood-Brain Barrier," *Soc. Neurosci.*, 2000, Abstract No. 26(2).

* cited by examiner

METHOD FOR ADMINISTERING A CYTOKINE TO THE CENTRAL NERVOUS SYSTEM AND THE LYMPHATIC SYSTEM

CROSS-REFERENCE TO RELATED APPLICATIONS

This application is a continuation of U.S. application Ser. No. 09/733,168, filed Dec. 8, 2000, which claims the benefit of U.S. Provisional Application No. 60/200,708, filed Dec. 9, 1999, which are herein incorporated in their entirety by reference.

FIELD OF THE INVENTION

The present invention is directed to a method for delivering cytokines to the central nervous system and by the lymphatic system by way of a tissue innervated by the trigeminal nerve and/or olfactory nerve. Cytokines include tumor necrosis factors, interleukins, interferons, particularly β-interferon and its muteins such as IFN-$β_{ser17}$. Such a method of delivery can be useful in the treatment of central nervous system and/or brain disorders.

BACKGROUND OF THE INVENTION

The central nervous system (CNS) includes several tissues and organs, such as the brain, the brain stem, and the spinal cord. Each of these organs and tissues is made up of a variety of different types of cells and subcellular structures, e.g., neurons, glial cells, dendrites, axons, myelin, and various membranes. The CNS is isolated from the external world by several membranes that both cushion and protect these organs, tissues, cells, and structures. For example, the membranes that form the blood-brain barrier protect the brain from certain contents of the blood. The blood-cerebrospinal fluid barrier protects other portions of the CNS from many chemicals and microbes.

Access to the CNS for some substances is provided by specialized active transport systems or through passive diffusion through the protective membrane into the CNS. Present methods for delivering desired therapeutic agents to the CNS are typically invasive. For example, a pump implanted into the chest cavity (an intracerebroventricular pump) can effectively deliver a variety of useful compounds to the brain. However, implanting such a pump requires surgery, which can entail a variety of serious complications. Certain compounds (e.g., epidural painkillers) can be injected directly through the protective membrane into the CNS. Such injection is, however, impractical for most medications. Better methods for administering desired agents to the CNS, brain, spinal cord, and lymphatic channels are needed.

SUMMARY OF THE INVENTION

The present invention relates to a method for transporting or delivering a cytokine, such as an interferon, an interleukin, or a tumor necrosis factor, preferably interferon-β, to the central nervous system of a subject. The method employs administration of the cytokine to a tissue innervated by the trigeminal nerve and/or olfactory nerve.

In one embodiment, the method administers the cytokine through the mucosa or epithelium of the nasal cavity, tongue, mouth, skin, or conjunctiva. In another embodiment, the method includes administering a composition of the cytokine to the nasal cavity, under the tongue, to the skin, or to the conjunctiva of the subject. The cytokine can then be absorbed through a mucosa or epithelium and transported to the central nervous system of the mammal.

In another embodiment, the method includes administering the cytokine in a manner such that the cytokine is absorbed through the tissue and transported into the central nervous system of the mammal by a neural pathway and in an amount effective to provide a protective or therapeutic effect on a cell of the central nervous system.

The present invention further relates to a method for transporting or delivering a cytokine, such as an interferon, an interleukin, or a tumor necrosis factor, preferably interferon-β, to the lymphatic system of a subject. The method employs administration of the cytokine to a tissue innervated by the trigeminal nerve and/or olfactory nerve.

In another embodiment, the method includes administering the cytokine in a manner such that the cytokine is absorbed through the tissue and transported into the central nervous system of the mammal by a neural pathway and in an amount effective to modulate an immune or inflammatory response.

In other embodiments, the method of administering a cytokine is used for the treatment and/or prevention of central nervous system disorders, brain disorders, proliferative, viral, and/or autoimmune disorders.

The composition can be of any form suitable for administration by these routes and can include a carrier that facilitates absorption of the cytokine, transport of the cytokine by a neural pathway, and/or transport of the cytokine to the lymphatic system, CNS, brain, and/or spinal cord. Preferred compositions include one or more of a solubility enhancing additive, a hydrophilic additive, an absorption promoting additive, a cationic surfactant, a viscosity enhancing additive, or a sustained release matrix or composition, a lipid-based carrier, preferably a micellar or liposomal composition, a bilayer destabilizing additive, or a fusogenic additive. The composition can be formulated as a cosmetic for dermal delivery.

DETAILED DESCRIPTION OF THE INVENTION

Routes of Administration

Figure 1:
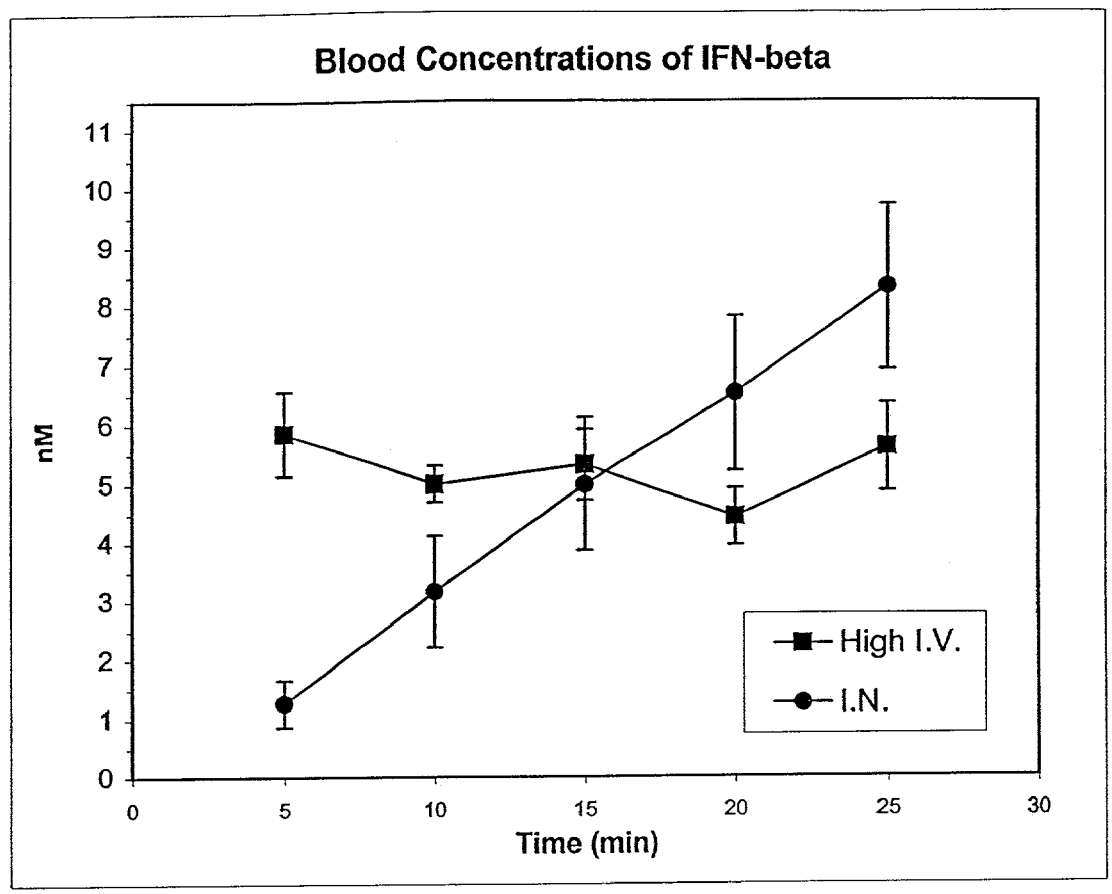
FIG. 1 shows the level of BETASERON® in the blood stream over time following both intravenous administration (I.V.) and intranasal administration (I.N.) in a rat.

The method of the invention administers the cytokine to tissue innervated by the trigeminal and olfactory nerves. Such nerve systems can provide a direct connection between the outside environment and the brain, thus providing advantageous delivery of a cytokine to the CNS, including brain, brain stem, and/or spinal cord. Cytokines are unable to cross or inefficiently cross the blood-brain barrier from the bloodstream into the brain. The methods of the present invention allow for the delivery of the cytokine by way of the olfactory and/or trigeminal nerve rather than through the circulatory system. This method of administration allows for the efficient delivery of a cytokine to the CNS, brain, or spinal cord.

The Olfactory Nerve

The method of the invention includes administration of a cytokine to tissue innervated by the olfactory nerve. Preferably, the cytokine is delivered to the olfactory area in the upper third of the nasal cavity and particularly to the olfactory epithelium.

Fibers of the olfactory nerve are unmyelinated axons of olfactory receptor cells that are located in the superior one-third of the nasal mucosa. The olfactory receptor cells are bipolar neurons with swellings covered by hair-like cilia that project into the nasal cavity. At the other end, axons from these cells collect into aggregates and enter the cranial cavity at the roof of the nose. Surrounded by a thin tube of pia, the olfactory nerves cross the subarachnoid space containing CSF and enter the inferior aspects of the olfactory bulbs. Once the cytokine is dispensed into the nasal cavity, the cytokine can undergo transport through the nasal mucosa and into the olfactory bulb and interconnected areas of the brain, such as the hippocampal formation, amygdaloid nuclei, nucleus basalis of Meynert, locus ceruleus, the brain stem, and the like.

The Trigeminal Nerve

The method of the invention administers the cytokine to tissue innervated by the trigeminal nerve. The trigeminal nerve innervates tissues of a mammal's (e.g., human) head including skin of the face and scalp, oral tissues, and tissues of and surrounding the eye. The trigeminal nerve has three major branches, the ophthalmic nerve, the maxillary nerve, and the mandibular nerve. The method of the invention can administer the cytokine to tissue innervated by one or more of these branches.

The Ophthalmic Nerve and its Branches

The method of the invention can administer the cytokine to tissue innervated by the ophthalmic nerve branch of the trigeminal nerve. The ophthalmic nerve innervates tissues including superficial and deep parts of the superior region of the face, such as the eye, the lacrimal gland, the conjunctiva, and skin of the scalp, forehead, upper eyelid, and nose.

The ophthalmic nerve has three branches known as the nasociliary nerve, the frontal nerve, and the lacrimal nerve. The method of the invention can administer the cytokine to tissue innervated by the one or more of the branches of the ophthalmic nerve. The frontal nerve and its branches innervate tissues including the upper eyelid, the scalp, particularly the front of the scalp, and the forehead, particularly the middle part of the forehead. The nasociliary nerve forms several branches including the long ciliary nerves, the ganglionic branches, the ethmoidal nerves, and the infratrochlear nerve. The long ciliary nerves innervate tissues including the eye. The posterior and anterior ethmoidal nerves innervate tissues including the ethmoidal sinus and the inferior two-thirds of the nasal cavity. The infratrochlear nerve innervates tissues including the upper eyelid and the lacrimal sack. The lacrimal nerve innervates tissues including the lacrimal gland, the conjunctiva, and the upper eyelid. Preferably, the present method administers the cytokine to the ethmoidal nerve.

The Maxillary Nerve and its Branches

The method of the invention can administer the cytokine to tissue innervated by the maxillary nerve branch of the trigeminal nerve. The maxillary nerve innervates tissues including the roots of several teeth and facial skin, such as skin on the nose, the upper lip, the lower eyelid, over the cheekbone, over the temporal region. The maxillary nerve has branches including the infraorbital nerve, the zygomaticofacial nerve, the zygomaticotemporal nerve, the nasopalatine nerve, the greater palatine nerve, the posterior superior alveolar nerves, the middle superior alveolar nerve, and the interior superior alveolar nerve. The method of the invention can administer the cytokine to tissue innervated by the one or more of the branches of the maxillary nerve.

The infraorbital nerve innervates tissue including skin on the lateral aspect of the nose, upper lip, and lower eyelid. The zygomaticofacial nerve innervates tissues including skin of the face over the zygomatic bone (cheekbone). The zygomaticotemporal nerve innervates tissue including the skin over the temporal region. The posterior superior alveolar nerves innervate tissues including the maxillary sinus and the roots of the maxillary molar teeth. The middle superior alveolar nerve innervates tissues including the mucosa of the maxillary sinus, the roots of the maxillary premolar teeth, and the mesiobuccal root of the first molar tooth. The anterior superior alveolar nerve innervates tissues including the maxillary sinus, the nasal septum, and the roots of the maxillary central and lateral incisors and canine teeth. The nasopalantine nerve innervates tissues including the nasal septum. The greater palatine nerve innervates tissues including the lateral wall of the nasal cavity. Preferably, the present method administers the cytokine to the nasopalatine nerve and/or greater palatine nerve.

The Mandibular Nerve and its Branches

The method of the invention can administer the cytokine to tissue innervated by the mandibular nerve branch of the trigeminal nerve. The mandibular nerve innervates tissues including the teeth, the gums, the floor of the oral cavity, the tongue, the cheek, the chin, the lower lip, tissues in and around the ear, the muscles of mastication, and skin including the temporal region, the lateral part of the scalp, and most of the lower part of the face.

The mandibular nerve has branches including the buccal nerve, the auriculotemporal nerve, the inferior alveolar nerve, and the lingual nerve. The method of the invention can administer the cytokine to one or more of the branches of the mandibular nerve. The buccal nerve innervates tissues including the cheek, particularly the skin of the cheek over the buccinator muscle and the mucous membrane lining the cheek, and the mandibular buccal gingiva (gum), in particular the posterior part of the buccal surface of the gingiva. The auriculotemporal nerve innervates tissues including the auricle, the external acoustic meatus, the tympanic membrane (eardrum), and skin in the temporal region, particularly the skin of the temple and the lateral part of the scalp. The inferior alveolar nerve innervates tissues including the mandibular teeth, in particular the incisor teeth, the gingiva adjacent the incisor teeth, the mucosa of the lower lip, the skin of the chin, the skin of the lower lip, and the labial mandibular gingivae. The lingual nerve innervates tissues including the tongue, particularly the anterior two-thirds of the tongue, the floor of the mouth, and the gingivae of the mandibular teeth. Preferably, the method of the invention administers the cytokine to one or more of the inferior alveolar nerve, the buccal nerve, and/or the lingual nerve.

Tissues Innervated by the Trigeminal Nerve

The method of the invention can administer the cytokine to any of a variety of tissues innervated by the trigeminal nerve. For example, the method can administer the cytokine to skin, epithelium, or mucosa of or around the face, the eye, the oral cavity, the nasal cavity, the sinus cavities, or the ear.

Preferably, the method of the invention administers the cytokine to skin innervated by the trigeminal nerve. For example, the present method can administer the cytokine to skin of the face, scalp, or temporal region. Suitable skin of the face includes skin of the chin; the upper lip, the lower lip; the forehead, particularly the middle part of the forehead; the nose, including the tip of the nose, the dorsum of the nose, and the lateral aspect of the nose; the cheek, particularly the skin of the cheek over the buccinator muscle or skin over the cheek bone; skin around the eye, particularly the upper eyelid and the lower eyelid; or a combination thereof. Suitable skin of the scalp includes the front of the scalp, scalp over the temporal region, the lateral part of the scalp, or a combination thereof. Suitable skin of the temporal region includes the temple and scalp over the temporal region.

Preferably, the method of the invention administers the cytokine to mucosa or epithelium innervated by the trigeminal nerve. For example, the present method can administer the cytokine to mucosa or epithelium of or surrounding the eye, such as mucosa or epithelium of the upper eyelid, the lower eyelid, the conjunctiva, the lacrimal system, or a combination thereof. The method of the invention can also administer the cytokine to mucosa or epithelium of the sinus cavities and/or nasal cavity, such as the inferior two-thirds of the nasal cavity and the nasal septum. The method of the invention can also administer the cytokine to mucosa or epithelium of the oral cavity, such as mucosa or epithelium of the tongue; particularly the anterior two-thirds of the tongue and under the tongue; the cheek; the lower lip; the upper lip; the floor of the oral cavity; the gingivae (gums), in particular the gingiva adjacent the incisor teeth, the labial mandibular gingivae, and the gingivae of the mandibular teeth; or a combination thereof. Preferably, the method of the invention administers the cytokine to mucosa or epithelium of the nasal cavity. Other preferred regions of mucosa or epithelium for administering the cytokine include the tongue, particularly sublingual mucosa or epithelium, the conjunctiva, the lacrimal system, particularly the palpebral portion of the lacrimal gland and the nasolacrimal ducts, the mucosa of the lower eyelid, the mucosa of the cheek, or a combination thereof.

Preferably, the method of the invention administers the cytokine to nasal tissues innervated by the trigeminal nerve. For example, the present method can administer the cytokine to nasal tissues including the sinuses, the inferior two-thirds of the nasal cavity and the nasal septum. Preferably, the nasal tissue for administering the cytokine includes the inferior two-thirds of the nasal cavity and the nasal septum.

Preferably, the method of the invention administers the cytokine to oral tissues innervated by the trigeminal nerve. For example, the present method can also administer the cytokine to oral tissues such as the teeth, the gums, the floor of the oral cavity, the cheeks, the lips, the tongue, particularly the anterior two-thirds of the tongue, or a combination thereof. Suitable teeth include mandibular teeth, such as the incisor teeth. Suitable portions of the teeth include the roots of several teeth, such as the roots of the maxillary molar teeth, the maxillary premolar teeth, the maxillary central and lateral incisors, the canine teeth, and the mesiobuccal root of the first molar tooth, or a combination thereof. Suitable portions of the lips include the skin and mucosa of the upper and lower lips. Suitable gums include the gingiva adjacent the incisor teeth and the gingivae of the mandibular teeth, such as the labial mandibular gingivae, or a combination thereof. Suitable portions of the cheek include the skin of the cheek over the buccinator muscle, the mucous membrane lining the cheek, and the mandibular buccal gingiva (gum), in particular the posterior part of the buccal surface of the gingiva, or a combination thereof. Preferred oral tissue for administering the cytokine includes the tongue, particularly sublingual mucosa or epithelium, the mucosa inside the lower lip, the mucosa of the cheek, or a combination thereof.

Preferably, the method of the invention administers the cytokine to a tissue of or around the eye that is innervated by the trigeminal nerve. For example, the present method can administer the cytokine to tissue including the eye, the conjunctiva, and the lacrimal gland including the lacrimal sack, the skin or mucosa of the upper or lower eyelid, or a combination thereof. Preferred tissue of or around the eye for administering the cytokine includes the conjunctiva, the lachrimal system, the skin or mucosa of the eyelid, or a combination thereof. Cytokine that is administered conjunctivally but not absorbed through the conjunctival mucosa can drain through nasolachrimal ducts into the nose, where it can be transported to the CNS, brain, and/or spinal cord as though it had been intranasally administered.

Preferably, the method of the invention administers the cytokine to a tissue of or around the ear that is innervated by the trigeminal nerve. For example, the present method can administer the cytokine to tissue including the auricle, the external acoustic meatus, the tympanic membrane (eardrum), and the skin in the temporal region, particularly the skin of the temple and the lateral part of the scalp, or a combination thereof. Preferred tissue of or around the ear for administering the cytokine includes the skin of the temple.

Cytokines

Cytokines can be administered to the CNS, brain, and/or spinal cord according to the present invention. Cytokines that can be administered by the method of the invention are cytokines that are immunomodulators, such as interleukins (i.e., IL-1, IL-2, IL-3, IL-4, IL-5, IL-6, IL-7, IL-8, IL-9 and IL-10), interferons, and tumor necrosis factor (i.e., TNF-α and TNF-β), and that have activities directed at cells of the immune system. These cytokines are of interest as therapeutic cytokines, for example, for treatment of viral diseases and control of cancer. It is believed that such cytokines have not been observed to have neurotrophic activity, or to have other direct, beneficial effects on neurons characteristic of nerve growth factor and like compounds. Thus, it was not expected that such cytokines should be transported into the CNS, brain, and or spinal cord, particularly not by a neural pathway, or from tissues innervated by the olfactory and/or trigeminal nerves.

A preferred cytokine for use in the practice of the invention are members of the interferon family. Interferons (IFNs) are a family of molecules encompassing over 20 different proteins and are members of the cytokine family that induce antiviral, antiproliferative, antitumor, and/or cytokine effects. IFNs are relatively small, species-specific, single chain polypeptides, which are produced in response to a variety of inducers, such as mitogens, polypeptides, viruses, and the like. In humans, IFNs are produced in forms α, β, γ, ω, and τ. Synthetic interferons are also known in the art. See, for example, U.S. Pat. No. 6,114,145, herein incorporated by reference. Upon secretion from mammalian cells, interferon molecules bind to a receptor on the surface of a target cell and elicit a chain of events, which can alter the amount and activity of protein in the target cell. Such alterations can include, for example, changes in gene transcription or enzymatic activity. A preferred interferon for use in the practice of the invention is interferon-β (IFN-β), interferon-α (IFN-α), and interferon-γ (IFN-γ).

Biologically active variants of cytokines are also encompassed by the method of the present invention. Such variants should retain the biological activity of the cytokine. For example, when the cytokine is an interferon, such as IFN-α, IFN-β, IFN-γ, the ability to bind their respective receptor sites will be retained. Such activity may be measured using standard bioassays. Representative assays detecting the ability of the variant to interact with an interferon receptor type I can be found in, for example, U.S. Pat. No. 5,766,864, herein incororpated by reference. Preferably, the variant has at least the same activity as the native molecule. Alternatively, the biological activity of a variant of the cytokine of the invention can be assayed by measuring the ability of the variant to increase viral resistance in a cell line using a standard viral reduction assay. See for example, U.S. Pat. No. 5,770,191, herein incorporated by reference. Other assays for biological activity include, anti-proliferative assays as described in U.S. Pat. No. 5,690,925.

Suitable biologically active variants can be fragments, analogues, and derivatives of the cytokine polypeptides. By "fragment" is intended a protein consisting of only a part of the intact cytokine polypeptide sequence. The fragment can be a C-terminal deletion or N-terminal deletion of the cytokine polypeptide. By "analogue" is intended an analogue of either the full length polypeptide having biological activity or a fragment thereof, that includes a native sequence and structure having one or more amino acid substitutions, insertions, or deletions. Peptides having one or more peptoids (peptide mimics) are also encompassed by the term analogue (see i.e., International Publication No. WO 91/04282). By "derivative" is intended any suitable modification of the native polypeptide or fragments thereof, or their respective analogues, such as glycosylation, phosphorylation, or other addition of foreign moieties, so long as the activity is retained.

Preferably, naturally or non-naturally occurring variants of a cytokine have amino acid sequences that are at least 70%, preferably 80%, more preferably, 85%, 90%, 91%, 92%, 93%, 94% or 95% identical to the amino acid sequence to the reference molecule, for example, the native human interferon, or to a shorter portion of the reference interferon molecule. More preferably, the molecules are 96%, 97%, 98% or 99% identical. Percent sequence identity is determined using the Smith-Waterman homology search algorithm using an affine gap search with a gap open penalty of 12 and a gap extension penalty of 2, BLOSUM matrix of 62. The Smith-Waterman homology search algorithm is taught in Smith and Waterman, *Adv. Appl. Math.* (1981) 2:482–489. A variant may, for example, differ by as few as 1 to 10 amino acid residues, such as 6–10, as few as 5, as few as 4, 3, 2, or even 1 amino aid residue.

With respect to optimal alignment of two amino acid sequences, the contiguous segment of the variant amino acid sequence may have additional amino acid residues or deleted amino acid residues with respect to the reference amino acid sequence. The contiguous segment used for comparison to the reference amino acid sequence will include at least 20 contiguous amino acid residues, and may be 30, 40, 50, or more amino acid residues. Corrections for sequence identity associated with conservative residue substitutions or gaps can be made (see Smith-Waterman homology search algorithm).

The art provides substantial guidance regarding the preparation and use of such variants, as discussed further below. A fragment of a cytokine polypeptide will generally include at least about 10 contiguous amino acid residues of the full-length molecule, preferably about 15–25 contiguous amino acid residues of the full-length molecule, and most preferably about 20–50 or more contiguous amino acid residues of full-length cytokine polypeptide.

For example, conservative amino acid substitutions may be made at one or more predicted, preferably nonessential amino acid residues. A "nonessential" amino acid residue is a residue that can be altered from the wild-type sequence of a cytokine, such as an interferon (i.e., IFN-α, IFN-β, or IFN-γ) without altering its biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Such substitutions would not be made for conserved amino acid residues, or for amino acid residues residing within a conserved motif.

Alternatively, variant cytokine nucleotide sequences can be made by introducing mutations randomly along all or part of a cytokine coding sequence, such as by saturation mutagenesis, and the resultant mutants can be screened for cytokine biological activity to identify mutants that retain activity. Following mutagenesis, the encoded protein can be expressed recombinantly, and the activity of the protein can be determined using standard assay techniques described herein.

Alternatively, the cytokine can be synthesized chemically, by any of several techniques that are known to those skilled in the peptide art. See, for example, Li et al. (1983) *Proc. Natl. Acad. Sci. USA* 80:2216–2220, Steward and Young (1984) *Solid Phase Peptide Synthesis* (Pierce Chemical Company, Rockford, Ill.), and Baraney and Merrifield (1980) *The Peptides: Analysis, Synthesis, Biology*, ed. Gross and Meinhofer, Vol. 2 (Academic Press, New York, 1980), pp. 3–254, discussing solid-phase peptide synthesis techniques; and Bodansky (1984) *Principles of peptide Synthesis* (Springer-Verlag, Berlin) and Gross and Meinhofer, eds. (1980) *The Peptides: Analysis, Synthesis, Biology*, Vol. 1 (Academic Press, New York), discussing classical solution synthesis. The cytokine can also be chemically prepared by the method of simultaneous multiple peptide synthesis. See, for example, Houghten (1984) *Proc. Natl. Acad. Sci. USA* 82:5131–5135; and U.S. Pat. No. 4,631,211.

The cytokine used in the methods of the invention can be from any animal species including, but not limited to, avian, canine, bovine, porcine, equine, and human. Preferably, the cytokine is from a mammalian species when the cytokine is to be used in treatment of a mammalian viral, immunomodulatory, or neurologic disorder of the CNS, brain or spinal cord, and more preferably is from a mammal of the same species as the mammal undergoing treatment for such a disorder.

Interferon-β

The term "IFN-β" as used herein refers to IFN-β or variants thereof, sometimes referred to as IFN-β-like polypeptides. Human IFN-β variants, which may be naturally occurring (e.g., allelic variants that occur at the IFN-β locus) or recombinantly produced, have amino acid sequences that are the same as, similar to, or substantially similar to the mature native IFN-β sequence. DNA sequences encoding human IFN-β are also available in the art. See, for example, Goeddel et al. (1980) *Nucleic Acid Res.* 8:4057 and Tanigachi et al. (1979) *Proc. Japan Acad. Sci.* 855:464. Fragments of IFN-β or truncated forms of IFN-β that retain their activity are also encompassed. These biologically active fragments or truncated forms of IFN-β are generated by removing amino acid residues from the full-length IFN-β amino acid sequence using recombinant DNA techniques well known in the art. IFN-β polypeptides may be glycosylated or unglycosylated, as it has been reported in the literature that both the glycosylated and unglycosylated forms of IFN-β show qualitatively similar specific activities and that, therefore, the glycosyl moieties are not involved in and do not contribute to the biological activity of IFN-β.

The IFN-β variants encompassed herein include muteins of the native mature IFN-β sequence, wherein one or more cysteine residues that are not essential to biological activity have been deliberately deleted or replaced with other amino acids to eliminate sites for either intermolecular crosslinking or incorrect intramolecular disulfide bond formation. IFN-β variants of this type include those containing a glycine, valine, alanine, leucine, isoleucine, tyrosine, phenylalanine, histidine, tryptophan, serine, threonine, or methionine substituted for the cysteine found at amino acid 17 of the mature native amino acid sequence. Serine and threonine are the more preferred replacements because of their chemical analogy to cysteine. Serine substitutions are most preferred. For example, an IFN-β variant can comprise a serine residue replacing the cysteine found at amino acid 17 of the mature native sequence. Cysteine 17 may also be deleted using methods known in the art (see, for example, U.S. Pat. No. 4,588,585, herein incorporated by reference), resulting in a mature IFN-β mutein that is one amino acid shorter than the native mature IFN-β. Thus, IFN-β variants with one or more mutations that improve, for example, their pharmaceutical utility are also encompassed by the present invention.

The skilled artisan will appreciate that additional changes can be introduced by mutation into the nucleotide sequences encoding IFN-β, thereby leading to changes in the IFN-β amino acid sequence, without altering the biological activity of the interferon. Thus, an isolated nucleic acid molecule encoding an IFN-β variant having a sequence that differs from human IFN-β can be created by introducing one or more nucleotide substitutions, additions, or deletions into the corresponding nucleotide sequence disclosed herein, such that one or more amino acid substitutions, additions or deletions are introduced into the encoded IFN-β. Mutations can be introduced by standard techniques, such as site-directed mutagenesis and PCR-mediated mutagenesis. Such IFN-β variants are also encompassed by the present invention. Variants of IFN-β are described in European Patent Application No. 18545981, and U.S. Pat. Nos. 4,518,584, 4,588,585, and 4,737,462, all of which are incorporated herein by reference.

Biologically active IFN-β variants encompassed by the invention also include IFN-β polypeptides that have covalently linked with, for example, polyethylene glycol (PEG) or albumin.

Biologically active variants of IFN-β encompassed by the invention should retain IFN-β activities, particularly the ability to bind to IFN-β receptors or retain immunomodulatory or anti-viral activities. In some embodiments, the IFN-β variant retains at least about 25%, about 50%, about 75%, about 85%, about 90%, about 95%, about 98%, about 99% or more of the biological activity of the native IFN-β polypeptide. IFN-β variants whose activity is increased in comparison with the activity of the native IFN-β polypeptide are also encompassed. The biological activity of IFN-β variants can be measured by any method known in the art. Examples of such assays can be found in Fellous et al. (1982) *Proc. Natl. Acad. Sci USA* 79:3082–3086; Czemiecki et al. (1984) *J. Virol.* 49(2):490–496; Mark et al. (1984) *Proc. Natl Acad. Sci. USA* 81:5662–5666; Branca et al. (1981) *Nature* 277:221–223; Williams et al. (1979) *Nature* 282:582–586; Herberman et al. (1979) *Nature* 277:221–223; and Anderson et al. (1982) *J. Biol. Chem.* 257(19):11301–11304.

Non-limiting examples of IFN-β polypeptides and IFN-β variant polypeptides encompassed by the invention are set forth in Nagata et al. (1980) *Nature* 284:316–320; Goeddel et al. (1980) *Nature* 287:411–416; Yelverton et al. (1981) *Nucleic Acids Res.* 9:731–741; Streuli et al. (1981) *Proc. Natl. Acad. Sci. U.S.A.* 78:2848–2852; EP028033B1, and EP109748B1. See also U.S. Pat. Nos. 4,518,584; 4,569,908; 4,588,585; 4,738,844; 4,753,795; 4,769,233; 4,793,995; 4,914,033; 4,959,314; 5,545,723; and 5,814,485. These disclosures are herein incorporated by reference. These citations also provide guidance regarding residues and regions of the IFN-β polypeptide that can be altered without the loss of biological activity.

In one embodiment of the present invention, the IFN-β used in the methods of the invention is the mature native human IFN-β polypeptide. In another embodiment, the IFN-β is the mature IFN-β C17S polypeptide. However, the present invention encompasses other embodiments where the IFN-β is any biologically active IFN-β polypeptide or variant as described elsewhere herein.

In some embodiments of the present invention, the IFN-β is recombinantly produced. By "recombinantly produced IFN-β" is intended IFN-β that has comparable biological activity to native IFN-β and that has been prepared by recombinant DNA techniques. IFN-β can be produced by culturing a host cell transformed with an expression vector comprising a nucleotide sequence that encodes an IFN-β polypeptide. The host cell is one that can transcribe the nucleotide sequence and produce the desired protein, and can be prokaryotic (for example, *E. coli*) or eukaryotic (for example a yeast, insect, or mammalian cell). Examples of recombinant production of IFN-β are given in Mantei et al. (1982) *Nature* 297:128; Ohno et al. (1982) *Nucleic Acids Res.* 10:967; Smith et al. (1983) *Mol. Cell. Biol.* 3:2156, and U.S. Pat. Nos. 4,462,940, 5,702,699, and 5,814,485; herein incorporated by reference.

Interferon-α

The term "IFN-α" as used herein refers to IFN-α or variants thereof, sometimes referred to as IFN-α-like polypeptides. Human alpha interferons comprise a family of about 30 protein species, encoded by at least 14 different genes and about 16 alleles. Such IFN-α polypeptides include IFN-αa, IFN-αB, IFN-αC, IFN-αD, IFN-αH, IFN-αJ, IFN-αJ1, IFN-αJ2 and IFN-αK. Human IFN-α variants, which may be naturally occurring (e.g., allelic variants that occur at the IFN-α locus) or recombinantly produced, have amino acid sequences that are the same as, similar to, or substantially similar to the mature native IFN-α sequence. DNA sequences encoding human IFN-α are also available in the art. See, for example, Goeddel et al. (1981) *Nature* 290: 20–26 (Genbank Accession No. V00551 J00209); Nagata et al. (1980) *Nature* 284:3126–320; Bowden et al. (1984) *Gene* 27:87–99 (Genbank Accession No. NM_000605); and Ohara et al. (1987) *FEBS Letters* 211:78–82; all of which are herein incorporated by reference. Fragments of IFN-α or truncated forms of IFN-α that retain their activity are also encompassed. These biologically active fragments or truncated forms of IFN-α are generated by removing amino acid residues from the full-length IFN-α amino acid sequence using recombinant DNA techniques well known in the art. IFN-α polypeptides may further be glycosylated or unglycosylated.

The skilled artisan will appreciate that additional changes can be introduced by mutation into the nucleotide sequences encoding IFN-α, thereby leading to changes in the IFN-α amino acid sequence, without altering the biological activity of the interferon. Thus, an isolated nucleic acid molecule encoding an IFN-α variant having a sequence that differs from human IFN-α can be created by introducing one or more nucleotide substitutions, additions, or deletions into the corresponding nucleotide sequence disclosed herein, such that one or more amino acid substitutions, additions or deletions are introduced into the encoded IFN-α. Mutations can be introduced by standard techniques. Such variants of IFN-α, include, for example, IFN-α-2a (ROFERON-A™), IFN-α-2b (INTRON A™), and IFN-αcon-1 (INFERGEN™). Another variant useful in the methods of the present invention is IFN-α2a, which is disclosed in, for example, EP 43980; Meada et al. (1980) *PNAS* 77:7010; and Levy et al. (1981) *PNAS* 78:6186; all of which are herein incorporated by reference. Further, variants of IFN-α can be found, for example, in U.S. Pat. No. 5,676,942, herein incorporated by reference. These citations also provide guidance regarding residues and regions of the IFN-α polypeptide that can be altered without the loss of biological activity.

Biologically active IFN-α variants encompassed by the invention also include IFN-α polypeptides that have covalently linked with, for example, polyethylene glycol (PEG) or albumin. See, for example, U.S. Pat. No. 5,762,923, herein incorporated by reference.

Biologically active variants of IFN-α encompassed by the invention should retain IFN-α activities, particularly the ability to bind to IFN-α receptors or retain immunomodulatory, antiviral, or anit-proliferative activities. In some embodiments, the IFN-α variant retains at least about 25%, about 50%, about 75%, about 85%, about 90%, about 95%, about 98%, about 99% or more of the biological activity of the native IFN-α polypeptide. IFN-α variants whose activity is increased in comparison with the activity of the native IFN-α polypeptide are also encompassed. The biological activity of IFN-α variants can be measured by any method known in the art. Examples of such assays are described above.

In one embodiment of the present invention, the IFN-α used in the methods of the invention is the mature native human IFN-α polypeptide. However, the present invention encompasses other embodiments where the IFN-α is any biologically active IFN-α polypeptide or variant as described elsewhere herein.

In some embodiments of the present invention, the IFN-α is recombinantly produced. By "recombinantly produced IFN-α" is intended IFN-α that has comparable biological activity to native IFN-α and that has been prepared by recombinant DNA techniques. IFN-α can be produced by culturing a host cell transformed with an expression vector comprising a nucleotide sequence that encodes an IFN-α polypeptide. The host cell is one that can transcribe the nucleotide sequence and produce the desired protein, and can be prokaryotic (for example, *E. coli*) or eukaryotic (for example a yeast, insect, or mammalian cell). Details of the cloning of interferon-cDNA and the direct expression thereof, especially in *E. coli*, have in the meantime been the subject of many publications. Thus, for example, the preparation of recombinant interferons is known. See, for example, (1982) *Nature* 295: 503–508; (1980) *Nature* 284: 316–320; (1981) *Nature* 290: 20–26; (1980) *Nucleic Acids Res.* 8: 4057–4074, as well as from European Patents Nos. 32134, 43980 and 211 148. Further examples of recombinant production of IFN-α-2 are provided in Nagata et al. (1980) *Nature* 284:316 and European Patent 32,134. All of these references are herein incorporated by reference.

Interferon-γ

The term "IFN-γ" as used herein refers to IFN-γ or variants thereof, sometimes referred to as IFN-γ-like polypeptides. IFN-γ is a glycoprotein whose mature form has 143 amino acids and a molecular weight of about 63–73 kilodaltons. The amino acid sequence of IFN-γ can be found in, for example, U.S. Pat. No. 6,046,034, herein incorporated by reference. Human IFN-γ variants, which may be naturally occurring (e.g., allelic variants that occur at the IFN-γ locus) or recombinantly produced, have amino acid sequences that are the same as, similar to, or substantially similar to the mature native IFN-γ sequence. DNA sequences encoding human IFN-γ are also available in the art. See, for example, Grey et al. (1983) *Proc. Natl. Acad. Sci. USA* 80:5842–5846, herein incorporated by reference. Fragments of IFN-γ or truncated forms of IFN-γ that retain their activity are also encompassed. These biologically active fragments or truncated forms of IFN-γ are generated by removing amino acid residues from the full-length IFN-γ amino acid sequence using recombinant DNA techniques well known in the art. IFN-γ polypeptides may be glycosylated or unglycosylated.

The IFN-γ variants encompassed herein include muteins of the native mature IFN-γ sequence. Thus, IFN-γ variants with one or more mutations that improve, for example, their pharmaceutical utility are also encompassed by the present invention.

Such IFN-γ variants are also encompassed by the present invention. Variants of IFN-γ are well known in the art. For example, U.S. Pat. No. 5,770,191, herein incorporated by reference, discloses peptides comprising the C-terminus of IFN-γ that retain the biological activity of the mature IFN-γ. Additionally, in EP 0 306870 A2, variants of human IFN-γ were identified whose activity was significantly increased by deleting the C-terminal 7–11 amino acids. In addition, WO 92-08737 discloses a variant of recombinant human IFN-γ (IFN-γ C-10 L) that has increased biological activity. Further variants of IFN-γ can be found in, for example, U.S. Pat. No. 5,690,925 and U.S. Pat. No. 6,046,034 both of which provide guidance as to the amino acid substitutions and deletions that can be made in IFN-γ without losing biological activity. Each of these references is herein incorporated by reference. The above examples represent non-limiting examples of IFN-γ polypeptides and IFN-γ variant polypeptides encompassed by the invention. These citations also provide guidance regarding residues and regions of the IFN-γ polypeptide that can be altered without the loss of biological activity.

Biologically active IFN-γ variants encompassed by the invention also include IFN-γ polypeptides that have covalently linked with, for example, polyethylene glycol (PEG) or albumin.

Biologically active variants of IFN-γ encompassed by the invention should retain IFN-γ activities, particularly the ability to bind to IFN-γ receptors or retain immunomodulatory, antiviral, or antiproliferative activities. In some embodiments, the IFN-γ variant retains at least about 25%, about 50%, about 75%, about 85%, about 90%, about 95%, about 98%, about 99% or more of the biological activity of the native IFN-γ polypeptide. IFN-γ variants whose activity is increased in comparison with the activity of the native IFN-γ polypeptide are also encompassed. The biological activity of IFN-γ variants can be measured by any method known in the art. Examples of such assays are described above.

In one embodiment of the present invention, the IFN-γ used in the methods of the invention is the mature native human IFN-γ polypeptide. However, the present invention encompasses other embodiments where the IFN-γ is any biologically active IFN-γ polypeptide or variant as described elsewhere herein.

In some embodiments of the present invention, the IFN-γ is recombinantly produced. By "recombinantly produced IFN-γ" is intended IFN-γ that has comparable biological activity to native IFN-γ and that has been prepared by recombinant DNA techniques. IFN-γ can be produced by culturing a host cell transformed with an expression vector comprising a nucleotide sequence that encodes an IFN-γ polypeptide. The host cell is one that can transcribe the nucleotide sequence and produce the desired protein, and can be prokaryotic (for example, $E.\ coli$) or eukaryotic (for example a yeast, insect, or mammalian cell). Examples of recombinant production of IFN-γ are given in 6,046,034 and 5,690,925; both of which are herein incorporated by reference.

Pharmaceutical Composition

Increases in the amount of cytokine in the CNS, brain, and/or spinal cord to a therapeutically effective level may be obtained via administration of a pharmaceutical composition including a therapeutically effective dose of this cytokine. By "therapeutically effective dose" is intended a dose of cytokine that achieves the desired goal of increasing the amount of this cytokine in a relevant portion of the CNS, brain, and/or spinal cord to a therapeutically effective level enabling a desired biological activity of the cytokine.

The invention is, in particular, directed to a composition that can be employed for delivery of a cytokine to the CNS, brain, and/or spinal cord upon administration to tissue innervated by the olfactory and/or trigeminal nerves. The composition can include, for example, any pharmaceutically acceptable additive, carrier, or adjuvant that is suitable for administering a cytokine to tissue innervated by the olfactory and/or trigeminal nerves. Preferably, the pharmaceutical composition can be employed in diagnosis, prevention, or treatment of a disease, disorder, or injury of the CNS, brain, and/or spinal cord. Preferably, the composition includes a cytokine in combination with a pharmaceutical carrier, additive, and/or adjuvant that can promote the transfer of the cytokine within or through tissue innervated by the olfactory and/or trigeminal nerves. Alternatively, the cytokine may be combined with substances that may assist in transporting the cytokine to sites of nerve cell damage. The composition can include one or several cytokines.

The composition typically contains a pharmaceutically acceptable carrier mixed with the cytokine and other components in the pharmaceutical composition. By "pharmaceutically acceptable carrier" is intended a carrier that is conventionally used in the art to facilitate the storage, administration, and/or the healing effect of the cytokine. A carrier may also reduce any undesirable side effects of the cytokine. A suitable carrier should be stable, i.e., incapable of reacting with other ingredients in the formulation. It should not produce significant local or systemic adverse effect in recipients at the dosages and concentrations employed for treatment. Such carriers are generally known in the art.

Suitable carriers for this invention include those conventionally used for large stable macromolecules such as albumin, gelatin, collagen, polysaccharide, monosaccharides, polyvinylpyrrolidone, polylactic acid, polyglycolic acid, polymeric amino acids, fixed oils, ethyl oleate, liposomes, glucose, sucrose, lactose, mannose, dextrose, dextran, cellulose, mannitol, sorbitol, polyethylene glycol (PEG), and the like.

Water, saline, aqueous dextrose, and glycols are preferred liquid carriers, particularly (when isotonic) for solutions. The carrier can be selected from various oils, including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions can be subjected to conventional pharmaceutical expedients, such as sterilization, and can contain conventional pharmaceutical additives, such as preservatives, stabilizing cytokines, wetting, or emulsifying agents, salts for adjusting osmotic pressure, buffers, and the like.

A composition formulated for intranasal delivery may optionally comprise an odorant. An odorant agent is combined with the cytokine to provide an odorliferous sensation, and/or to encourage inhalation of the intranasal preparation to enhance delivery of the active cytokine to the olfactory neuroepithelium. The odorliferous sensation provided by the odorant agent may be pleasant, obnoxious, or otherwise malodorous. The odorant receptor neurons are localized to the olfactory epithelium that, in humans, occupies only a few square centimeters in the upper part of the nasal cavity. The cilia of the olfactory neuronal dendrites which contain the receptors are fairly long (about 30–200 um). A 10–30 $\mu$m layer of mucus envelops the cilia that the odorant agent must penetrate to reach the receptors. See Snyder et al. (1998) $J$ $Biol.\ Chem.$ 263:13972–13974. Use of a lipophillic odorant agent having moderate to high affinity for odorant binding protein (OBP) is preferred. OBP has an affinity for small lipophillic molecules found in nasal secretions and may act as a carrier to enhance the transport of a lipophillic odorant substance and cytokines to the olfactory receptor neurons. It is also preferred that an odorant agent is capable of associating with lipophillic additives such as liposomes and micelles within the preparation to further enhance delivery of the cytokines by means of OBP to the olfactory neuroepithelium. OBP may also bind directly to lipophillic agents to enhance transport of the cytokines to olfactory neural receptors.

Suitable odorants having a high affinity for OBP include terpanoids such as cetralva and citronellol, aldehydes such as amyl clnnamaldehyde and hexyl cinnamaldehyde, esters such as octyl isovalerate, jasmines such as C1S-jasmine and jasmal, and musk 89. Other suitable odorant agents include those which may be capable of stimulating odorant-sensitive enzymes such as aderrylate cyclase and guanylate cyclase, or which may be capable of modifying ion channels within the olfactory system to enhance absorption of the cytokine.

Other acceptable components in the composition include, but are not limited to, pharmaceutically acceptable agents that modify isotonicity, including water, salts, sugars, polyols, amino acids and buffers, such as, phosphate, citrate, succinate, acetate, and other organic acids or their salts. Typically, the pharmaceutically acceptable carrier also includes one or more stabilizers, reducing agents, anti-oxidants and/or anti-oxidant chelating agents. The use of buffers, stabilizers, reducing agents, anti-oxidants and chelating agents in the preparation of protein based compositions, particularly pharmaceutical compositions, is well known in the art. See Wang et al. (1980) *J. Parent. Drug Assn.,* 34(6):452–462; Wang et al. (1988) *J. Parent. Sci. and Tech.* 42:S4–S26 (Supplement); Lachman, et al. (1968) *Drug and Cosmetic Industry,* 102(1): 36–38, 40 and 146–148; Akers, M. J. (1988) *J. Parent. Sci. and Tech.,* 36(5):222–228; and Colowick et al. *Methods in Enzymology,* Vol. XXV, p. 185–188.

Suitable buffers include acetate, adipate, benzoate, citrate, lactate, maleate, phosphate, tartarate, borate, tri(hydroxymethyl aminomethane), succinate, glycine, histidine, the salts of various amino acids, or the like, or combinations thereof. See Wang (1980) supra at page 455. Suitable salts and isotonicifiers include sodium chloride, dextrose, mannitol, sucrose, trehalose, or the like. Where the carrier is a liquid, it is preferred that the carrier is hypotonic or isotonic with oral, conjunctival or dermal fluids and have a pH within the range of 4.5–8.5. Where the carrier is in powdered form, it is preferred that the carrier is also within an acceptable non-toxic pH range.

Suitable reducing agents, which maintain the reduction of reduced cysteines, include dithiothreitol (DTT also known as Cleland's reagent) or dithioerythritol at 0.01% to 0.1% wt/wt; acetylcysteine or cysteine at 0.1% to 0.5% (pH 2–3); and thioglycerol at 0.1% to 0.5% (pH 3.5 to 7.0) and glutathione. See Akers (1988) supra at pages 225 to 226. Suitable antioxidants include sodium bisulfite, sodium sulfite, sodium metabisulfite, sodium thiosulfate, sodium formaldehyde sulfoxylate, and ascorbic acid. See Akers (1988) supra at pages 225. Suitable chelating agents, which chelate trace metals to prevent the trace metal catalyzed oxidation of reduced cysteines, include citrate, tartarate, ethylenediaminetetraacetic acid (EDTA) in its disodium, tetrasodium, and calcium disodium salts, and diethylenetriamine pentaacetic acid (DTPA). See, e.g., Wang (1980) supra at pages 457–458 and 460–461, and Akers (1988) supra at pages 224–227.

The composition can include one or more preservatives such as phenol, cresol, p-aminobenzoic acid, BDSA, sorbitrate, chlorhexidine, benzalkonium chloride, or the like. Suitable stabilizers include carbohydrates such as trehalose or glycerol. The composition can include a stabilizer such as one or more of microcrystalline cellulose, magnesium stearate, mannitol, sucrose to stabilize, for example, the physical form of the composition; and one or more of glycine, arginine, hydrolyzed collagen, or protease inhibitors to stabilize, for example, the chemical structure of the composition. Suitable suspending additives include carboxymethyl cellulose, hydroxypropyl methylcellulose, hyaluronic acid, alginate, chondroitin sulfate, dextran, maltodextrin, dextran sulfate, or the like. The composition can include an emulsifier such as polysorbate 20, polysorbate 80, pluronic, triolein, soybean oil, lecithins, squalene and squalanes, sorbitan treioleate, or the like. The composition can include an antimicrobial such as phenylethyl alcohol, phenol, cresol, benzalkonium chloride, phenoxyethanol, chlorhexidine, thimerosol, or the like. Suitable thickeners include natural polysaccharides such as mannans, arabinans, alginate, hyaluronic acid, dextrose, or the like; and synthetic ones like the PEG hydrogels of low molecular weight and aforementioned suspending cytokines.

The composition can include an adjuvant such as cetyl trimethyl ammonium bromide, BDSA, cholate, deoxycholate, polysorbate 20 and 80, fusidic acid, or the like, and in the case of DNA delivery, preferably, a cationic lipid.

Suitable sugars include glycerol, threose, glucose, galactose, mannitol, and sorbitol. A suitable protein is human serum albumin.

Preferred compositions include one or more of a solubility enhancing additive, preferably a cyclodextrin; a hydrophilic additive, preferably a monosaccharide or oligosaccharide; an absorption promoting additive, preferably a cholate, a deoxycholate, a fusidic acid, or a chitosan; a cationic surfactant, preferably a cetyl trimethyl ammonium bromide; a viscosity enhancing additive, preferably to promote residence time of the composition at the site of administration, preferably a carboxymethyl cellulose, a maltodextrin, an alginic acid, a hyaluronic acid, or a chondroitin sulfate; or a sustained release matrix, preferably a polyanhydride, a polyorthoester, a hydrogel, a particulate slow release depo system, preferably a polylactide co-glycolides (PLG), a depo foam, a starch microsphere, or a cellulose derived buccal system; a lipid-based carrier, preferably an emulsion, a liposome, a niosomes, or a micelles. The composition can include a bilayer destabilizing additive, preferably a phosphatidyl ethanolamine; a fusogenic additive, preferably a cholesterol hemisuccinate.

Other preferred compositions for sublingual administration including, for example, a bioadhesive to retain the cytokine sublingually; a spray, paint, or swab applied to the tongue; retaining a slow dissolving pill or lozenge under the tongue; or the like. Other preferred compositions for transdermal administration include a bioadhesive to retain the cytokine on or in the skin; a spray, paint, cosmetic, or swab applied to the skin; or the like.

These lists of carriers and additives is by no means complete and a worker skilled in the art can choose excipients from the GRAS (generally regarded as safe) list of chemicals allowed in the pharmaceutical preparations and those that are currently allowed in topical and parenteral formulations.

For the purposes of this invention, the pharmaceutical composition comprising the cytokine can be formulated in a unit dosage and in a form such as a solution, suspension, or emulsion. The cytokine may be administered to tissue innervated by the trigeminal and/or olfactory neurons as a powder, a granule, a solution, a cream, a spray (e.g., an aerosol), a gel, an ointment, an infusion, an injection, a drop, or sustained-release composition, such as a polymer disk. For buccal administration, the compositions can take the form of tablets or lozenges formulated in a conventional manner. For administration to the eye or other external tissues, e.g., mouth and skin, the compositions can be applied to the infected part of the body of the patient as a topical ointment or cream. The compounds can be presented in an ointment, for instance with a water-soluble ointment base, or in a cream, for instance with an-oil-in water cream base. For conjunctival applications, the cytokine can be administered in biodegradable or non-degradable ocular inserts. The drug may be released by matrix erosion or passively through a pore as in ethylene-vinylacetate polymer inserts. For other mucosal administrations, such as sublingual, powder discs may be placed under the tongue and active delivery systems may for in situ by slow hydration as in the formulation of liposomes from dried lipid mixtures or pro-liposomes.

Other preferred forms of compositions for administration include a suspension of a particulate, such as an emulsion, a liposome, an insert that releases the cytokine slowly, and the like. The powder or granular forms of the pharmaceutical composition may be combined with a solution and with a diluting, dispersing, or surface-active cytokine. Additional preferred compositions for administration include a bioadhesive to retain the cytokine at the site of administration; a spray, paint, or swab applied to the mucosa or epithelium; a slow dissolving pill or lozenge; or the like. The composition can also be in the form of lyophilized powder, which can be converted into a solution, suspension, or emulsion before administration. The pharmaceutical composition including cytokine is preferably sterilized by membrane filtration and is stored in unit-dose or multi-dose containers such as sealed vials or ampoules.

The method for formulating a pharmaceutical composition is generally known in the art. A thorough discussion of formulation and selection of pharmaceutically acceptable carriers, stabilizers, and isomolytes can be found in *Remington's Pharmaceutical Sciences* ($18^{th}$ ed.; Mack Publishing Company, Eaton, Pa., 1990), herein incorporated by reference.

The cytokine of the present invention can also be formulated in a sustained-release form to prolong the presence of the pharmaceutically active cytokine in the treated mammal, generally for longer than one day. Many methods of preparation of a sustained-release formulation are known in the art and are disclosed in *Remington's Pharmaceutical Sciences* (18th ed.; Mack Publishing Company, Eaton, Pa., 1990), herein incorporated by reference.

Generally, the cytokine can be entrapped in semipermeable matrices of solid hydrophobic polymers. The matrices can be shaped into films or microcapsules. Examples of such matrices include, but are not limited to, polyesters, copolymers of L-glutamic acid and gamma ethyl-L-glutamate (Sidman et al. (1983) *Biopolymers* 22:547–556), polylactides (U.S. Pat. No. 3,773,919 and EP 58,481), polylactate polyglycolate (PLGA) such as polylactide-co-glycolide (see, for example, U.S. Pat. Nos. 4,767,628 and 5,654,008), hydrogels (see, for example, Langer et al. (1981) *J. Biomed. Mater. Res.* 15:167–277; Langer (1982) *Chem. Tech.* 12:98–105), non-degradable ethylene-vinyl acetate (e.g. ethylene vinyl acetate disks and poly(ethylene-co-vinyl acetate)), degradable lactic acid-glycolic acid copolyers such as the Lupron Depot™, poly-D-(–)-3-hydroxybutyric acid (EP 133,988), hyaluronic acid gels (see, for example, U.S. Pat. No. 4,636,524), alginic acid suspensions, and the like.

Suitable microcapsules can also include hydroxymethylcellulose or gelatin-microcapsules and polymethyl methacrylate microcapsules prepared by coacervation techniques or by interfacial polymerization. See the PCT publication WO 99/24061 entitled "Method for Producing Sustained-release Formulations," wherein a protein is encapsulated in PLGA microspheres, herein incorporated by reference. In addition, microemulsions or colloidal drug delivery systems such as liposomes and albumin microspheres, may also be used. See *Remington's Pharmaceutical Sciences* ($18^{th}$ ed.; Mack Publishing Company Co., Eaton, Pa., 1990). Other preferred sustained-release compositions employ a bioadhesive to retain the cytokine at the site of administration.

Among the optional substances that may be combined with the cytokine in the pharmaceutical composition are lipophilic substances that can enhance absorption of the cytokine through the mucosa or epithelium of the nasal cavity, or along a neural, lymphatic, or perivascular pathway to damaged nerve cells in the CNS. The cytokine may be mixed with a lipophilic adjuvant alone or in combination with a carrier, or may be combined with one or several types of micelle or liposome substances. Among the preferred lipophilic substances are cationic liposomes included of one or more of the following: phosphatidyl choline, lipofectin, DOTAP, a lipid-peptoid conjugate, a synthetic phospholipid such as phosphatidyl lysine, or the like. These liposomes may include other lipophilic substances such as gangliosides and phosphatidylserine (PS). Also preferred are micellar additives such as GM-1 gangliosides and phosphatidylserine (PS), which may be combined with the cytokine either alone or in combination. GM-1 ganglioside can be included at 1–10 mole percent in any liposomal compositions or in higher amounts in micellar structures. Protein cytokines can be either encapsulated in particulate structures or incorporated as part of the hydrophobic portion of the structure depending on the hydrophobicity of the active cytokine.

One preferred liposomal formulation employs Depofoam. A cytokine can be encapsulated in multivesicular liposomes, as disclosed in the WO publication 99/12522 entitled "High and Low Load Formulations of IGF-I in Multivesicular Liposomes," herein incorporated by reference. The mean residence time of cytokine at the site of administration can be prolonged with a Depofoam composition.

Administering the Cytokine

According to this embodiment of the invention, the total amount of cytokine administered per dose should be in a range sufficient to delivery a biologically relevant amount of the cytokine (i.e., an amount sufficient to produce a therapeutical effect). The pharmaceutical composition having a unit dose of cytokine can be in the form of solution, suspension, emulsion, or a sustained-release formulation. The total volume of one dose of the pharmaceutical composition can range from about 10 µl to about 100 µl, for example, for nasal administration. It is apparent that the suitable volume can vary with factors such as the size of the tissue to which the cytokine is administered and the solubility of the components in the composition.

It is recognized that the total amount of cytokine administered as a unit dose to a particular tissue will depend upon the type of pharmaceutical composition being administered, that is whether the composition is in the form of, for example, a solution, a suspension, an emulsion, or a sustained-release formulation. For example, where the pharmaceutical composition comprising a therapeutically effective amount of cytokine is a sustained-release formulation, cytokine is administered at a higher concentration. Needle-free subcutaneous administration to an extranasal tissue innervated by the trigeminal nerve may be accomplished by use of a device which employs a supersonic gas jet as a power source to accelerate an agent that is formulated as a powder or a microparticle into the skin. The characteristics of such a delivery method will be determined by the properties of the particle, the formulation of the agent and the gas dynamics of the delivery device. Similarly, the subcutaneous delivery of an aqueous composition can be accomplished in a needle-free manner by employing a gas-spring powered hand held device to produce a high force jet of fluid capable of penetrating the skin. Alternatively, a skin-patch formulated to mediate a sustained release of a composition can be employed for the transdermal delivery of a neuroregulatory agent to a tissue innervated by the trigeminal nerve. Where the pharmaceutical composition comprises a therapeutically effective amount of an agent, or a combination of agents, in a sustained-release formulation, the agent(s) is/are administered at a higher concentration.

It should be apparent to a person skilled in the art that variations may be acceptable with respect to the therapeutically effective dose and frequency of the administration a cytokine in this embodiment of the invention. The amount of the cytokine administered will be inversely correlated with the frequency of administration. Hence, an increase in the concentration of cytokine in a single administered dose, or an increase in the mean residence time in the case of a sustained-release form of cytokine, generally will be coupled with a decrease in the frequency of administration.

In the practice of the present invention, additional factors should be taken into consideration when determining the therapeutically effective dose of cytokine and frequency of its administration. Such factors include, for example, the size of the tissue, the area of the surface of the tissue, the severity of the disease or disorder, and the age, height, weight, health, and physical condition of the individual to be treated. Generally, a higher dosage is preferred if the tissue is larger or the disease or disorder is more severe.

Some minor degree of experimentation may be required to determine the most effective dose and frequency of dose administration, this being well within the capability of one skilled in the art once apprised of the present disclosure.

For the treatment of a disorder of the CNS in a human, including neurologic, viral, proliferative or immunomodulatory disorders, a therapeutically effective amount or dose of a cytokine is about 0.14 nmol/kg of brain weight to about 138 nmol/kg brain weight and about 0.14 nmol/kg of brain weight to about 69 nmol/kg of brain weight. In some regimens, therapeutically effective doses for administration of a cytokine include about 0.13, 0.2, 0.4, 0.6, 0.8, 1.0, 10, 20, 30, 40, 50, 60, 70, 80, 90, 100, 110, 120, 130, or 140 nmoles per kg of brain weight. For the treatment of a disorder of the CNS in a human, including neurologic, viral, proliferative or immunomodulatory disorders, the therapeutically effective amount or dose of IFN-β or biologically active variant thereof is about 0.14 nmol/kg of brain weight to about 138 nmol/kg of brain weight and about 0.14 nmol/kg of brain weight to about 69 nmol/kg of brain weight. In some regimens, therapeutically effective doses for administration of IFN-β include about 0.13, 0.2, 0.4, 0.6, 0.8, 1.0, 10, 20, 30, 40, 50, 60, 70, 80, 90, 100, 110, 120, 130, or 140 nmoles per kg of brain weight.

It is further recognized that the therapeutically effective amount or dose of a cytokine to a human may be lower when the cytokine is administered via the nasal lymphatics to various tissues of the head and neck for the treatment or prevention of disorders or diseases characterized by immune and inflammatory responses (i.e., diseases resulting in acute or chronic inflammation and/or infiltration by lymphocytes). In these embodiments, while the cytokine can be administered in the dosage range provided above, the cytokine may also be administered from about 0.02 to about 138 pmol/kg of brain weight. Alternatively, the cytokine may be administered from about 0.02, 0.03, 0.08, 0.1, 0.2, 0.3, 0.4, 0.5, 0.6, 0.7, 0.8, 0.9, 1, 10, 20, 30, 40, 50, 60, 70, 80, 90, 100, 110, 120, 130, or 140 pmol per kg of brain weight. Similarly, when the cytokine is IFN-β, the dosage range may also be from about 0.02 to about 138 pmol/kg of brain weight. Alternatively, the cytokine maybe administered from about 0.02, 0.03, 0.08, 0.1, 0.2, 0.3, 0.4, 0.5, 0.6, 0.7, 0.8, 0.9, 1, 10, 20, 30, 40, 50, 60, 70, 80, 90, 100, 110, 120, 130, or 140 pmol per kg of brain weight.

These doses depend on factors including the efficiency with which cytokine IFN-β is transported to the CNS or lymphatic system. A larger total dose can be delivered by multiple administrations of the agent.

Intermittent Dosing

In another embodiment of the invention, the pharmaceutical composition comprising the therapeutically effective dose of cytokine is administered intermittently. By "intermittent administration" is intended administration of a therapeutically effective dose of cytokine, followed by a time period of discontinuance, which is then followed by another administration of a therapeutically effective dose, and so forth. Administration of the therapeutically effective dose may be achieved in a continuous manner, as for example with a sustained-release formulation, or it may be achieved according to a desired daily dosage regimen, as for example with one, two, three or more administrations per day. By "time period of discontinuance" is intended a discontinuing of the continuous sustained-released or daily administration of cytokine. The time period of discontinuance may be longer or shorter than the period of continuous sustained-release or daily administration. During the time period of discontinuance, the cytokine level in the relevant tissue is substantially below the maximum level obtained during the treatment. The preferred length of the discontinuance period depends on the concentration of the effective dose and the form of cytokine used. The discontinuance period can be at least 2 days, preferably is at least 4 days, more preferably is at least 1 week and generally does not exceed a period of 4 weeks. When a sustained-release formulation is used, the discontinuance period must be extended to account for the greater residence time of cytokine at the site of injury. Alternatively, the frequency of administration of the effective dose of the sustained-release formulation can be decreased accordingly. An intermittent schedule of administration of cytokine can continue until the desired therapeutic effect, and ultimately treatment of the disease or disorder, is achieved.

In yet another embodiment, intermittent administration of the therapeutically effective dose of cytokine is cyclic. By "cyclic" is intended intermittent administration accompanied by breaks in the administration, with cycles ranging from about 1 month to about 2, 3, 4, 5, or 6 months. For example, the administration schedule might be intermittent administration of the effective dose of cytokine, wherein a single short-term dose is given once per week for 4 weeks, followed by a break in intermittent administration for a period of 3 months, followed by intermittent administration by administration of a single short-term dose given once per week for 4 weeks, followed by a break in intermittent administration for a period of 3 months, and so forth. As another example, a single short-term dose may be given once per week for 2 weeks, followed by a break in intermittent administration for a period of 1 month, followed by a single short-term dose given once per week for 2 weeks, followed by a break in intermittent administration for a period of 1 month, and so forth. A cyclic intermittent schedule of administration of cytokine to subject may continue until the desired therapeutic effect, and ultimately treatment of the disorder or disease, is achieved.

Neuronal Transport

One embodiment of the present method includes administration of the cytokine to the subject in a manner such that the cytokine is transported to the lymphatic system, the lacrimal gland, CNS, brain, and/or spinal cord along a neural pathway. A neural pathway includes transport within or along a neuron, through or by way of lymphatics running with a neuron, through or by way of a perivascular space of a blood vessel running with a neuron or neural pathway, through or by way of an adventitia of a blood vessel running with a neuron or neural pathway, or through an hemangiolymphatic system. The invention prefers transport of a cytokine by way of a neural pathway, rather than through the circulatory system, so that cytokines that are unable to, or only poorly, cross the blood-brain barrier from the bloodstream into the brain can be delivered to the lymphatic system, CNS, brain, and/or spinal cord. The cytokine, once past the blood-brain barrier and in the CNS, can then be delivered to various areas of the brain or spinal cord through lymphatic channels, through a perivascular space, or transport through or along neurons. In one embodiment, the cytokine preferably accumulates in areas having the greatest density of receptor or binding sites for that cytokine.

Use of a neural pathway to transport a cytokine to the lymphatic system, lacrimal gland, brain, spinal cord, or other components of the central nervous system obviates the obstacle presented by the blood-brain barrier so that medications that cannot normally cross that barrier, can be delivered directly to the brain, cerebellum, brain stem, or spinal cord. Although the cytokine that is administered may be absorbed into the bloodstream as well as the neural pathway, the cytokine preferably provides minimal effects systemically. In addition, the invention can provide for delivery of a more concentrated level of the cytokine to neural cells since the cytokine does not become diluted in fluids present in the bloodstream. As such, the invention provides an improved method for delivering a cytokine to the lymphatic system, CNS, brain, and/or spinal cord.

The Olfactory Neural Pathway

One embodiment of the present method includes delivery of the cytokine to the subject in a manner such that the cytokine is transported into the CNS, brain, and/or spinal cord along an olfactory neural pathway. Typically, such an embodiment includes administering the cytokine to tissue innervated by the olfactory nerve and inside the nasal cavity. The olfactory neural pathway innervates primarily the olfactory epithelium in the upper third of the nasal cavity, as described above. Application of the cytokine to a tissue innervated by the olfactory nerve can deliver the cytokine to damaged neurons or cells of the CNS, brain, and/or spinal cord. Olfactory neurons innervate this tissue and can provide a direct connection to the CNS, brain, and/or spinal cord due, it is believed, to their role in olfaction.

Delivery through the olfactory neural pathway can employ lymphatics that travel with the olfactory nerve to the various brain areas and from there into dural lymphatics associated with portions of the CNS, such as the spinal cord. Transport along the olfactory nerve can also deliver cytokines to an olfactory bulb. A perivascular pathway and/or a hemangiolymphatic pathway, such as lymphatic channels running within the adventitia of cerebral blood vessels, can provide an additional mechanism for transport of therapeutic cytokines to the brain and spinal cord from tissue innervated by the olfactory nerve.

A cytokine can be administered to the olfactory nerve, for example, through the olfactory epithelium. Such administration can employ extracellular or intracellular (e.g., transneuronal) anterograde and retrograde transport of the cytokine entering through the olfactory nerves to the brain and its meninges, to the brain stem, or to the spinal cord. Once the cytokine is dispensed into or onto tissue innervated by the olfactory nerve, the cytokine may transport through the tissue and travel along olfactory neurons into areas of the CNS including the brain stem, cerebellum, spinal cord, olfactory bulb, and cortical and subcortical structures.

Delivery through the olfactory neural pathway can employ movement of a cytokine into or across mucosa or epithelium into the olfactory nerve or into a lymphatic, a blood vessel perivascular space, a blood vessel adventitia, or a blood vessel lymphatic that travels with the olfactory nerve to the brain and from there into meningial lymphatics associated with portions of the CNS such as the spinal cord. Blood vessel lymphatics include lymphatic channels that are around the blood vessels on the outside of the blood vessels. This also is referred to as the hemangiolymphatic system. Introduction of a cytokine into the blood vessel lymphatics does not necessarily introduce the cytokine into the blood.

The Trigeminal Neural Pathway

One embodiment of the present method includes delivery of the cytokine to the subject in a manner such that the cytokine is transported into the CNS, brain, and/or spinal cord along a trigeminal neural pathway. Typically, such an embodiment includes administering the cytokine to tissue innervated by the trigeminal nerve including inside and outside the nasal cavity. The trigeminal neural pathway innervates various tissues of the head and face, as described above. In particular, the trigeminal nerve innervates the nasal, sinusoidal, oral and conjunctival mucosa or epithelium, and the skin of the face. Application of the cytokine to a tissue innervated by the trigeminal nerve can deliver the cytokine to damaged neurons or cells of the CNS, brain, and/or spinal cord to cells of the lymphatic system. Trigeminal neurons innervate these tissues and can provide a direct connection to the CNS, brain, and/or spinal cord due, it is believed, to their role in the common chemical sense including mechanical sensation, thermal sensation and nociception (for example detection of hot spices and of noxious chemicals).

Delivery through the trigeminal neural pathway can employ lymphatics that travel with the trigeminal nerve to the pons and other brain areas and from there into dural lymphatics associated with portions of the CNS, such as the spinal cord. Transport along the trigeminal nerve can also deliver cytokines to an olfactory bulb. A perivascular pathway and/or a hemangiolymphatic pathway, such as lymphatic channels running within the adventitia of cerebral blood vessels, can provide an additional mechanism for transport of therapeutic cytokines to the spinal cord from tissue innervated by the trigeminal nerve.

The trigeminal nerve includes large diameter axons, which mediate mechanical sensation, e.g., touch, and small diameter axons, which mediate pain and thermal sensation, both of whose cell bodies are located in the semilunar (or trigeminal) ganglion or the mesencephalic trigeminal nucleus in the midbrain. Certain portions of the trigeminal nerve extend into the nasal cavity, oral and conjunctival mucosa and/or epithelium. Other portions of the trigeminal nerve extend into the skin of the face, forehead, upper eyelid, lower eyelid, dorsum of the nose, side of the nose, upper lip, cheek, chin, scalp and teeth. Individual fibers of the trigeminal nerve collect into a large bundle, travel underneath the brain and enter the ventral aspect of the pons. A cytokine can be administered to the trigeminal nerve, for example, through the nasal cavity's, oral, lingual, and/or conjunctival mucosa and/or epithelium; or through the skin of the face, forehead, upper eyelid, lower eyelid, dorsum of the nose, side of the nose, upper lip, cheek, chin, scalp and teeth. Such administration can employ extracellular or intracellular (e.g., transneuronal) anterograde and retrograde transport of the cytokine entering through the trigeminal nerves to the brain and its meninges, to the brain stem, or to the spinal cord. Once the cytokine is dispensed into or onto tissue innervated by the trigeminal nerve, the cytokine may transport through the tissue and travel along trigeminal neurons into areas of the CNS including the brain stem, cerebellum, spinal cord, olfactory bulb, and cortical and subcortical structures.

Delivery through the trigeminal neural pathway can employ movement of a cytokine across skin, mucosa, or epithelium into the trigeminal nerve or into a lymphatic, a blood vessel perivascular space, a blood vessel adventitia, or a blood vessel lymphatic that travels with the trigeminal nerve to the pons and from there into meningial lymphatics associated with portions of the CNS such as the spinal cord. Blood vessel lymphatics include lymphatic channels that are around the blood vessels on the outside of the blood vessels. This also is referred to as the hemangiolymphatic system. Introduction of a cytokine into the blood vessel lymphatics does not necessarily introduce the cytokine into the blood.

Neural Pathways and Nasal Administration

In one embodiment, the method of the invention can employ delivery by a neural pathway, e.g., a trigeminal or olfactory neural pathway, after administration to the nasal cavity. Upon administration to the nasal cavity, delivery via the trigeminal neural pathway may employ movement of a cytokine through the nasal mucosa and/or epithelium to reach a trigeminal nerve or a perivascular and/or lymphatic channel that travels with the nerve. Upon administration to the nasal cavity, delivery via the olfactory neural pathway may employ movement of a cytokine through the nasal mucosa and/or epithelium to reach the olfactory nerve or a perivascular and/or lymphatic channel that travels with the nerve.

For example, the cytokine can be administered to the nasal cavity in a manner that employs extracellular or intracellular (e.g., transneuronal) anterograde and retrograde transport into and along the trigeminal and/or olfactory nerves to reach the brain, the brain stem, or the spinal cord. Once the cytokine is dispensed into or onto nasal mucosa and/or epithelium innervated by the trigeminal and/or olfactory nerve, the cytokine may transport through the nasal mucosa and/or epithelium and travel along trigeminal and/or olfactory neurons into areas of the CNS including the brain stem, cerebellum, spinal cord, olfactory bulb, and cortical and subcortical structures. Alternatively, administration to the nasal cavity can result in delivery of a cytokine into a blood vessel perivascular space or a lymphatic that travels with the trigeminal and/or olfactory nerve to the pons, olfactory bulb, and other brain areas, and from there into meningeal lymphatics associated with portions of the CNS such as the spinal cord. Transport along the trigeminal and/or olfactory nerve may also deliver cytokines administered to the nasal cavity to the olfactory bulb, midbrain, diencephalon, medulla, and cerebellum. A cytokine administered to the nasal cavity can enter the ventral dura of the brain and travel in lymphatic channels within the dura.

In addition, the method of the invention can be carried out in a way that employs a perivascular pathway and/or an hemangiolymphatic pathway, such as a lymphatic channel running within the adventitia of a cerebral blood vessel, to provide an additional mechanism for transport of cytokine to the spinal cord from the nasal mucosa and/or epithelium. A cytokine transported by the hemangiolymphatic pathway does not necessarily enter the circulation. Blood vessel lymphatics associated with the circle of Willis as well as blood vessels following the trigeminal and/or olfactory nerve can also be involved in the transport of the cytokine.

Administration to the nasal cavity employing a neural pathway can deliver a cytokine to the lymphatic system, brain stem, cerebellum, spinal cord, and cortical and subcortical structures. The cytokine alone may facilitate this movement into the CNS, brain, and/or spinal cord. Alternatively, the carrier or other transfer-promoting factors may assist in the transport of the cytokine into and along the trigeminal and/or olfactory neural pathway. Administration to the nasal cavity of a therapeutic cytokine can bypass the blood-brain barrier through a transport system from the nasal mucosa and/or epithelium to the brain and spinal cord.

Neural Pathways and Transdermal Administration

In one embodiment, the method of the invention can employ delivery by a neural pathway, e.g., a trigeminal neural pathway, after transdermal administration. Upon transdermal administration, delivery via the trigeminal neural pathway may employ movement of a cytokine through the skin to reach a trigeminal nerve or a perivascular and/or lymphatic channel that travels with the nerve.

For example, the cytokine can be administered transdermally in a manner that employs extracellular or intracellular (e.g., transneuronal) anterograde and retrograde transport into and along the trigeminal nerves to reach the brain, the brain stem, or the spinal cord. Once the cytokine is dispensed into or onto skin innervated by the trigeminal nerve, the cytokine may transport through the skin and travel along trigeminal neurons into areas of the CNS including the brain stem, cerebellum, spinal cord, olfactory bulb, and cortical and subcortical structures. Alternatively, transdermal administration can result in delivery of a cytokine into a blood vessel perivascular space or a lymphatic that travels with the trigeminal nerve to the pons, olfactory bulb, and other brain areas, and from there into meningeal lymphatics associated with portions of the CNS such as the spinal cord. Transport along the trigeminal nerve may also deliver transdermally administered cytokines to the olfactory bulb, midbrain, diencephalon, medulla and cerebellum. The ethmoidal branch of the trigeminal nerve enters the cribriform region. An transdermally administered cytokine can enter the ventral dura of the brain and travel in lymphatic channels within the dura.

In addition, the method of the invention can be carried out in a way that employs a perivascular pathway and/or an hemangiolymphatic pathway, such as a lymphatic channel running within the adventitia of a cerebral blood vessel, to provide an additional mechanism for transport of cytokine to the spinal cord from the skin. A cytokine transported by the hemangiolymphatic pathway does not necessarily enter the circulation. Blood vessel lymphatics associated with the circle of Willis as well as blood vessels following the trigeminal nerve can also be involved in the transport of the cytokine.

Transdermal administration employing a neural pathway can deliver a cytokine to the brain stem, cerebellum, spinal cord and cortical and subcortical structures. The cytokine alone may facilitate this movement into the CNS, brain, and/or spinal cord. Alternatively, the carrier or other transfer-promoting factors may assist in the transport of the cytokine into and along the trigeminal neural pathway. Transdermal administration of a therapeutic cytokine can bypass the blood-brain barrier through a transport system from the skin to the brain and spinal cord.

Neural Pathways and Sublingual Administration

In another embodiment, the method of the invention can employ delivery by a neural pathway, e.g., a trigeminal neural pathway, after sublingual administration. Upon sublingual administration, delivery via the trigeminal neural pathway may employ movement of a cytokine from under the tongue and across the lingual epithelium to reach a trigeminal nerve or a perivascular or lymphatic channel that travels with the nerve.

For example, the cytokine can be administered sublingually in a manner that employs extracellular or intracellular (e.g., transneuronal) anterograde and retrograde transport through the oral mucosa and then into and along the trigeminal nerves to reach the brain, the brain stem, or the spinal cord. Once the cytokine is administered sublingually, the cytokine may transport through the oral mucosa by means of the peripheral processes of trigeminal neurons into areas of the CNS including the brain stem, spinal cord and cortical and subcortical structures. Alternatively, sublingual administration can result in delivery of a cytokine into lymphatics that travel with the trigeminal nerve to the pons and other brain areas and from there into meningeal lymphatics associated with portions of the CNS such as the spinal cord. Transport along the trigeminal nerve may also deliver sublingually administered cytokines to the olfactory bulbs, midbrain, diencephalon, medulla and cerebellum. The ethmoidal branch of the trigeminal nerve enters the cribriform region. A sublingually administered cytokine can enter the ventral dura of the brain and travel in lymphatic channels within the dura.

In addition, the method of the invention can be carried out in a way that employs an hemangiolymphatic pathway, such as a lymphatic channel running within the adventitia of a cerebral blood vessel, to provide an additional mechanism for transport of a cytokine to the spinal cord from the oral submucosa. A cytokine transported by the hemangiolymphatic pathway does not necessarily enter the circulation. Blood vessel lymphatics associated with the circle of Willis as well as blood vessels following the trigeminal nerve can also be involved in the transport of the cytokine.

Sublingual administration employing a neural pathway can deliver a cytokine to the brain stem, cerebellum, spinal cord and cortical and subcortical structures. The cytokine alone may facilitate this movement into the CNS, brain, and/or spinal cord. Alternatively, the carrier or other transfer-promoting factors may assist in the transport of the cytokine into and along the trigeminal neural pathway. Sublingual administration of a therapeutic cytokine can bypass the blood-brain barrier through a transport system from the oral mucosa to the brain and spinal cord.

Neural Pathways and Conjunctival Administration

In another embodiment, the method of the invention can employ delivery by a neural pathway, e.g. a trigeminal neural pathway, after conjunctival administration. Upon conjunctival administration, delivery via the trigeminal neural pathway may employ movement of a cytokine from the conjunctiva through the conjunctival epithelium to reach the trigeminal nerves or lymphatic channels that travel with the nerve.

For example, the cytokine can be administered conjunctivally in a manner that employs extracellular or intracellular (e.g., transneuronal) anterograde and retrograde transport through the conjunctival mucosa and then into and along the trigeminal nerves to reach the brain, the brain stem, or the spinal cord. Once the cytokine is administered conjunctivally, the cytokine may transport through the conjunctival mucosa by means of the peripheral processes of trigeminal neurons into areas of the CNS including the brain stem, spinal cord and cortical and subcortical structures. Alternatively, conjunctival administration can result in delivery of a cytokine into lymphatics that travel with the trigeminal nerve to the pons and other brain areas and from there into meningeal lymphatics associated with portions of the CNS such as the spinal cord. Transport along the trigeminal nerve may also deliver conjunctivally administered cytokines to the olfactory bulbs, midbrain, diencephalon, medulla and cerebellum. The ethmoidal branch of the trigeminal nerve enters the cribriform region. An conjunctivally administered cytokine can enter the ventral dura of the brain and travel in lymphatic channels within the dura.

In addition, the method of the invention can be carried out in a way that employs an hemangiolymphatic pathway, such as a lymphatic channel running within the adventitia of cerebral blood vessel, to provide an additional mechanism for transport of a cytokine to the spinal cord from the conjunctival submucosa. A cytokine transported by the hemangiolymphatic pathway does not necessarily enter the circulation. Blood vessel lymphatics associated with the circle of Willis as well as blood vessels following the trigeminal nerve can also be involved in the transport of the cytokine.

Conjunctival administration employing a neural pathway can deliver a cytokine to the brain stem, cerebellum, spinal cord and cortical and subcortical structures. The cytokine alone may facilitate this movement into the CNS, brain, and/or spinal cord. Alternatively, the carrier or other transfer-promoting factors may assist in the transport of the cytokine into and along the trigeminal neural pathway. Conjunctival administration of a therapeutic cytokine can bypass the blood-brain barrier through a transport system from the conjunctival mucosa to the brain and spinal cord.

Articles and Methods of Manufacture

The present invention also includes an article of manufacture providing a cytokine for administration to the CNS, brain, and/or spinal cord. The article of manufacture can include a vial or other container that contains a composition suitable for the present method together with any carrier, either dried or in liquid form. The article of manufacture further includes instructions in the form of a label on the container and/or in the form of an insert included in a box in which the container is packaged, for the carrying out the method of the invention. The instructions can also be printed on the box in which the vial is packaged. The instructions contain information such as sufficient dosage and administration information so as to allow the subject or a worker in the field to administer the cytokine. It is anticipated that a worker in the field encompasses any doctor, nurse, technician, spouse, or other care-giver that might administer the cytokine. The cytokine can also be self-administered by the subject.

According to the invention, a cytokine can be used for manufacturing a cytokine composition or medicament suitable for intranasal, conjunctival, transdermal, and/or sublingual administration. For example, a liquid or solid composition can be manufactured in several ways, using conventional techniques. A liquid composition can be manufactured by dissolving a cytokine in a suitable solvent, such as water, at an appropriate pH, including buffers or other excipients, for example to form a solution described herein above.

Disorders of the Central Nervous System

In one embodiment, the present method can be employed to deliver cytokines, particularly IFN-β, to the brain for diagnosis, treatment or prevention of disorders or diseases of the CNS, brain, and/or spinal cord. IFN-β increases the astrocytic production of nerve growth factor (NGF) (Boutros et al. (1997) *Journal of Neurochemistry* 69:939–946) and IFN-β sustains neuronal growth in cell culture (Plioplys et al. (1995) *Neuroimmunodulation* 2:131–135). IFN-β has therefore been associated with neurotrophic activity; hence, the methods of the present invention can be used for the delivery of a cytokine to the CNS to treat or prevent disorders or diseases of the CNS, brain, and/or spinal cord.

Disorders of the CNS, brain and/or spinal cord can be neurologic or psychiatric disorders, and include, for example, brain diseases such as Alzheimer's disease, Parkinson's disease, Lewy body dementia, multiple sclerosis, epilepsy, cerebellar ataxia, progressive supranuclear palsy, amyotrophic lateral sclerosis, affective disorders, anxiety disorders, obsessive compulsive disorders, personality disorders, attention deficit disorder, attention deficit hyperactivity disorder, Tourette Syndrome, Tay Sachs, Nieman Pick, and other lipid storage and genetic brain diseases and/or schizophrenia. The method can also be employed in subjects suffering from or at risk for nerve damage from cerebrovascular disorders such as stroke in the brain or spinal cord, from CNS infections including meningitis and HIV, from tumors of the brain and spinal cord, or from a prior disease. The method can also be employed to deliver cytokines to counter CNS disorders resulting from ordinary aging (e.g., anosmia or loss of the general chemical sense), brain injury, or spinal cord injury.

Multiple sclerosis is a preferred disease or disorder of the CNS, brain, and/or spinal cord. Despite its possible presence in the periphery, multiple sclerosis is a disease of the CNS. Accordingly, multiple sclerosis may be targeted more efficiently by a method delivering interferons to the CNS, brain and/or spinal cord.

Another preferred disease of the CNS, brain, and/or spinal cord is meningitis.

An "effective amount" of a cytokine is an amount sufficient to prevent, treat, reduce and/or ameliorate the symptoms and/or underlying causes of any of the above disorders or diseases discussed herein. In some instances, an "effective amount" is sufficient to eliminate the symptoms of those diseases and, perhaps, overcome the disease itself. In the context of the present invention, the terms "treat" and "therapy" and the like refer to alleviate, slow the progression, prophylaxis, attenuation or cure of existing disease. Prevent, as used herein, refers to delaying, slowing, inhibiting, reducing or ameliorating the onset of the CNS or brain diseases or disorders. It is preferred that a sufficient quantity of the cytokine be applied in non-toxic levels in order to provide an effective level of activity within the CNS to prevent or treat the disease. The method of the present invention may be used with any mammal. Exemplary mammals include, but are not limited to rats, cats, dogs, horses, cows, sheep, pigs, and more preferably humans.

Further Embodiments

Modulation of Immune and Inflammatory Responses

The method of cytokine administration provided by the present invention allows for the directed administration of the cytokine to the nasal lymphatic system. Following entry of the cytokine into the nasal lymphatics, the cytokine can be distributed throughout the lymphatics of the head and neck region. Hence, the method of the present invention can be employed to deliver cytokines to the lymphatic system including, for example, the deep and superficial cervical nodes, and to various tissues of the head and neck for the treatment or prevention of disorders or diseases characterized by immune and inflammatory responses (i.e., diseases resulting in acute or chronic inflammation and/or infiltration by lymphocytes). As such the present invention provides a method to modulate the immune response. By modulate is intended any up or down regulation of the immune or inflammatory response (i.e., influencing systemic immune function, antigen presentation, cytokine production, and entry of leukocytes into the CNS).

Of particular interest in the methods of the invention is the administration of IFN-β. IFN-β, like many of the interferons, reportedly serves as an immunomodulator on a number of target cells (Hall et al (1997) *J. Neuroimmunol.* 72:11–19). For instance, IFN-β appears to exert antiproliferative action on macrophages, counteract "the mitogenic stimulus of certain cytokines", augment natural killer cell activity to induce an increase in the production of cytotoxic T lymphocytes, and act on large, granular lymphocytes to increase killer cell activity. Additionally, IFN-β augments the proliferation of B cells and the secretion of IgM, IgG, and IgA. It has been shown to upregulate class I MHC expression to produce an increase in the presentation of class I restricted antigen CD8 cells (Hall et al. (1997) *J. Neuroimmunol.* 72:11–19). Conversely, IFN-β exerts an inhibitory effect on the upregulation of class II surface expression. Hence, the immunomodulatory activities of IFN-β include, for example, influencing systemic immune function, antigen presentation, cytokine production, and entry of leukocytes into the CNS (Yong et al. (1998) *Neurology* 51:582–689). Direct delivery of the cytokine to the lymphatics of the head and neck using the administration methods of the present invention allows the cytokine to modulate the immune response, i.e., influence chronic and acute inflammation, wound healing, and the autoimmune response; modulate the function by lymphocytes (reduce lymphocyte infiltration of the injured tissue); etc.

Given the immunomodulatory role of cytokines, the present invention can be employed to deliver cytokines, preferably IFN-β, to various tissues of the head and neck for the treatment and/or prevention of diseases or disorders characterized by immune and inflammatory responses. Disorders or diseases of particular interest include Multiple Sclerosis (MS), meningitis, and Primary Sjogren's Syndrome.

MS presents in the white matter of the CNS and spinal cord as a number of sclerotic lesions or plaques (Prineas (1985) *Demyelinating Diseases*, Elsvevier: Amsterdam; Raine (1983) *Multiple Sclerosis*, Williams and Wilkins: Baltimore; Raine et al. (1988) *J. Neuroimmunol.* 20:189–201; and Martin (1997) *J. Neural Transmission* (Suppl) 49:53–67). The characteristic MS lesion is inflamed, exhibits axonal demyelination, axonal degeneration, and is found around small venules. These characteristics typically evolve early in plaque development and are hypothesized to occur as a result of a breakdown in the blood-brain barrier (BBB). As a consequence of BBB breakdown, infiltrates consisting of various lymphocytes and macrophages enter the brain. The infiltrates cause a decrease in inflammation while increasing the presence of glial scar tissue, and elicit incomplete remyelination (Martin (1997) *J. Neural Transmission* (Suppl) 49:53–67). Further, it is hypothesized that this apparent immunologic attack targets not only the myelin sheath, but also the oligodendrocytes imperative to CNS myelin production. Cytokines are known to effectively reduce the symptoms of MS. For example, interferon-β (IFN-β has received interest as a treatment for relapsing-remitting MS. In addition, interest has also developed in the use of interferon-τ as an effective treatment in autoimmune diseases, such as MS. See, for example, U.S. Pat. No. 6,060,450, herein incorporated by reference.

The immunomodulating activity of IFN-β influences the clinical symptoms of MS. Hence, IFN-β can be administered according to the methods of the present invention to treat MS. While the present invention is not bound by the mechanism of IFN-β action, the central nervous system damage that ensues in MS patients is believed to be due to the delayed-type hypersensitivity response. This is a cell-mediated response. First, T cells are activated by antigens and conveyed to the lymphoid organ (activation). The lymphoid organ then activates these T cells while continuing to recruit more T cells to its site (recruitment). The activated lymphocytes proliferate and return to circulation (expansion). Once returned to circulation, the activated lymphocytes migrate through the blood stream, crossing endothelial cells lining the capillaries (migration). These migrating lymphocytes and macrophages target, and are attracted to the area of inflammation (attraction). Resulting from this attraction, other lymphocytes continue to the area of inflammation and tissue is destroyed (tissue destruction). Subsequently, the acute response is suppressed (via tissue destruction), and repair of the area of inflammation, which is quite limited in MS, may commence (repair) (Kelley (1996) *J. of Neuroscience Nursing* 28:114–120). Therefore, the migration of activated lymphocytes from the blood initiates the immune response, thereby allowing BBB penetration of activated lymphocytes.

Evidence suggests that the immunomodulatory activity of IFN-β inhibits IFN-γ upregulation by inhibiting the expansion stage of the delayed-type hypersensitivity response and thereby influences the clinical symptoms of MS. Particularly, the reduction of myelin damage appears to occur as a result of two hypothesized mechanisms of IFN-β action: (1) inhibition of IFN-γ-induced macrophage activation, and (2) inhibition of monocytotic TNF release (Kelly (1996) *J. Neuroscience Nursing* 28:114–120). Potential sites of IFN-β action construed by these hypotheses involve systemic immune function, antigen presentation, cytokine production, and entry of leukocytes into the CNS (Yong et al. (1998) *Neurology* 51:682–689). Each of these sites has been elaborated in human and animal experiments of MS.

An "effective amount" of a cytokine to treat MS using the administration methods of the present invention will be sufficient to reduce or lessen the clinical symptoms of MS. For instance, experimental allergic encephalomyelitis (EAE) is commonly used as an animal model of MS. A therapeutically effect amount of a cytokine delivered by the methods of the present invention will be such as to improve the clinical symptoms of EAE in the experimental animal (i.e., rats or mice). EAE in rats is scored on a scale of 0–4: 0, clinically normal; 1, flaccid tail paralysis; 2, hind limb weakness; 3, hind limb paralysis; 4, front and hind limb affected. An effective amount of cytokine delivered by the methods of the present invention will be effective if there is at least a 30%, 40%, 50% or greater reduction in the mean cumulative score over several days following the onset of disease symptoms in comparison to the control group.

Furthermore, effective treatment of MS may be examined in several alternative ways including, EDSS (extended disability status scale), appearance of exacerbations, or MRI. Satisfying any of the following criteria evidences effective treatment.

The EDSS is a means to grade clinical impairment due to MS (Kurtzke (1983) *Neurology* 33:1444). Eight functional systems are evaluated for the type and severity of neurologic impairment. Briefly, prior to treatment, impairment in the following systems is evaluated: pyramidal, cerebellar, brainstem, sensory, bowel and bladder, visual, cerebral, and other. Follow-ups are conducted at defined intervals. The scale ranges from 0 (normal) to 10 (death due to MS). A decrease of one full step defines an effective treatment in the context of the present invention (Kurtzke (1994) *Ann. Neurol.* 36:573–79).

Exacerbations are defined as the appearance of a new symptom that is attributable to MS and accompanied by an appropriate new neurologic abnormality (IFN-β MS Study Group, supra). In addition, the exacerbation must last at least 24 hours and be preceded by stability or improvement for at least 30 days. Standard neurological examinations result in the exacerbations being classified as either mild, moderate, or severe according to changes in a Neurological Rating Scale (Sipe et al. (1984) *Neurology* 34:1368). An annual exacerbation rate and proportion of exacerbation-free patients are determined. Therapy is deemed to be effective if there is a statistically significant difference in the rate or proportion of exacerbation-free patients between the treated group and the placebo group for either of these measurements. In addition, time to first exacerbation and exacerbation duration and severity may also be measured. A measure of effectiveness as therapy in this regard is a statistically significant difference in the time to first exacerbation or duration and severity in the treated group compared to control group.

MRI can be used to measure active lesions using gadolinium-DTPA-enhanced imaging (McDonald et al. (1994) *Ann. Neurol.* 36:14) or the location and extent of lesions using $T_2$-weighted techniques. Briefly, baseline MRIs are obtained. The same imaging plane and patient position are used for each subsequent study. Areas of lesions are outlined and summed slice by slice for total lesion area. Three analyses may be done: evidence of new lesions, rate of appearance of active lesions, and percentage change in lesion area (Paty et al. (1993) *Neurology* 43:665). Improvement due to therapy is established when there is a statistically significant improvement in an individual patient compared to baseline or in a treated group versus a placebo group.

It is further recognized that additional compounds can be administered with the cytokine to produce a therapeutic effect. For instance, IGF-1 has been implicated in preventing the depletion of mature oligodendrocytes and promoting recovery from demyelination in MS and other demyelinating disorders. See, for example, Mason et al. (2000) *J. Neuroscience* 20:5703–5708, herein incorporated by reference. Hence, IFN-β can be administered in conjunction with IGF-1 for the treatment of MS. The compounds can be administered by the methods of the invention. Alternatively, one of the compounds can be administered by any method known in the art including, for example, subcutaneous and intramuscular routes.

The IGF-1 used according to the methods of the present invention can be in its substantially purified, native, recombinantly produced, or chemically synthesized forms. For example, IGF-1 can be isolated directly from blood, such as from serum or plasma, by known methods. See, for example, Phillips (1980) *New Eng. J. Med.* 302:371–380; Svoboda et al. (1980) *Biochemistry* 19:790–797; Cornell and Boughdady (1982) *Prep. Biochem.* 12:57; Cornell and Boughdady (1984) *Prep. Biochem.* 14:123; European Patent No. EP 123,228; and U.S. Pat. No. 4,769,361. IGF-1 may also be recombinantly produced in the yeast strain *Pichia pastoris* and purified essentially as described in U.S. Pat. Nos. 5,324,639, 5,324,660, and 5,650,496 and International Publication No. WO 96/40776; all of which are herein incorporated by reference.

Alternatively, IGF-1 can be synthesized chemically, by any of several techniques that are known to those skilled in the peptide art. See, for example, Li et al. (1983) *Proc. Natl. Acad. Sci. USA* 80:2216–2220, Stewart and Young (1984) *Solid Phase Peptide Synthesis* (Pierce Chemical Company, Rockford, Ill.), and Barany and Merrifield (1980) *The Peptides: Analysis, Synthesis*, Biology, ed. Gross and Meienhofer, Vol. 2 (Academic Press, New York, 1980), pp. 3–254, for solid phase peptide synthesis techniques; and Bodansky (1984) Principles of Peptide Synthesis (Springer-Verlag, Berlin); and Gross and Meienhofer, eds. (1980) *The Peptides: Analysis*, Synthesis, Biology, Vol. 1 (Academic Press, New York), for classical solution synthesis. IGF-1 can also be chemically prepared by the method of simultaneous multiple peptide synthesis. See, for example, Houghten (1985) *Proc. Natl. Acad. Sci. USA* 82:5131–5135; and U.S. Pat. No. 4,631,211. These references are herein incorporated by reference. Furthermore, methods to prepare a highly concentrated, low salt-containing, biologically active form of IGF-1 or variant thereof are provided in WO 99/24062, entitled Novel IGF-1 Compositions and Its Use.

Methods for making IGF-1 fragments, analogues, and derivatives are available in the art. See generally U.S. Pat. Nos. 4,738,921, 5,158,875, and 5,077,276; International Publication Nos. WO 85/00831, WO 92/04363, WO 87/01038, and WO 89/05822; and European Patent Nos. EP 135094, EP 123228, and EP 128733; herein incorporated by reference.

In addition, several IGF-1 variants are known in the art and include those described in, for example, *Proc. Natl. Acad. Sci. USA* 83 (1986):4904–4907; *Biochem. Biophys. Res. Commun.* 149 (1987):398–404; *J. Biol. Chem.* 263 (1988):6233–6239; *Biochem. Biophys. Res. Commun.* 165 (1989):766–771; Forsbert et al. (1990) *Biochem. J.* 271: 357–363; U.S. Pat. Nos. 4,876,242 and 5,077,276; and International Publication Nos. WO 87/01038 and WO 89/05822. Representative variants include one with a deletion of Glu-3 of the mature molecule, a variant with up to 5 amino acids truncated from the N-terminus, a variant with a truncation of the first 3 N-terminal amino acids (referred to as des(1-3)-IGF-1, des-IGF-1, tIGF-1, or brain IGF), and a variant including the first 17 amino acids of the B chain of human insulin in place of the first 16 amino acids of human IGF-1.

Meningitis refers to an inflammatory process of the leptomeninges and CSF within the subarachnoid space. Meningoencephalitis applies to inflammation of the meninges and brain parenchyma. Meningitis is usually caused by an infection, but chemical meningitis may also occur in response to a non-bacterial irritant introduced into the subarachonoid space. Infiltration of the subarachnoid space by carcinoma is referred to as meningeal carcinomatosis and by lymphoma as lymphomapyogenic (usually bacterial), aseptic (usually viral), and chronic (most any infectious agent).

It has been suggested that the central nervous system damage that occurs in viral and bacterial meningitis may be more related to invasion of the surface of the brain by the host's own lymphocytes in response to the meningitis pathogen, rather than to the pathogen itself or any toxin produced by the pathogen (Lewis (1979) *The Medusa and The Snail*, Penguin Books). In fact, many patients fall victim to the disease despite the prompt sterilization of the cerebrospinal fluid using the current aggressive treatments, such as the third generation cephalosporins. This unexpected outcome may result from harmful interactions between host cells/ tissues and bacterial components released by treatment with lytic antibiotics (Scand et al. (1991) *J. Infect., Dis. Supp.* 74:173–179). The burst of peptidoglycan, capsular polysaccharide, and lipopolysaccharide liberated from the bacteria induce the production of a number of mediators including TNF in the central nervous system leading to meningeal and perivascular inflammation in the subarachnoid space. Disruption of the blood-brain barrier ensues, leading to cerebral edema, ischemia, and a dramatic increase in intracranial pressure. Those that survive the acute phase of the disease are often left with multiple neurological sequelae. Previous results from trials utilizing steroid-based anti-inflammatories either prior to or concomitant with antibiotic administration suggest that such an approach may have value. See, for example, Mustafa et al. (1990) *Amer. J. Diseases of Children* 144:883–887. Hence, administration of a cytokine, particularly interferon-β, using the methods of the present invention could be effective in preventing damage by activated lymphocytes. The methods of the invention could be used in conjunction with the existing treatments for meningitis to help prevent brain damage. Such treatments are described in *Harrion's Principles of Internal Medicine* (McGraw Hill, 1994), pp. 2296–2309, herein incorporated by reference.

An "effective amount" of a cytokine to treat meningitis using the administration method of the present invention will be sufficient to reduce or lessen the clinical symptoms of meningitis. In preferred embodiments, the cytokine is administered in conjunction with an antibiotic regiment. As such, an effective amount of the cytokine augments the activity of the antibiotics and leads to enhanced survival and/or improved clinical status of the animals in comparison to animals treated with antibiotics alone. Such clinical manifestations may include, for example, 1) a more rapid normalization of the CNS inflammatory indices compared to a control; 2) a more rapid disappearance in fever as compared to a control; 3) a reduction in the overall neurologic sequelae; and/or, 4) an improved mortality as compared to a control. More extensive details regarding the clinical manifestations of meningitis that can be improved upon the administration of an effective concentration of a cytokine can be found in *Harrion's Principles of Internal Medicine* (McGraw Hill, 1994), pp. 2296–2309, herein incorporated by reference.

Primary Sjogren's Syndrome, also known as Dry Eye Syndrome, is characterized by decreased secretion of the lacrimal glands that make the aqueous layer of the tear film that lubricates the eyes. Many patients afflicted with Sjogren's Syndrome also experience dry mouth due to decreased secretion of the salivary glands. This is an autoimmune disease characterized by chronic inflammation and infiltration of the lacrimal and salivary glands by lymphocytes. Activated T cells of the $CD4^+$ type that infiltrate the lacrimal gland mediate tissue destruction (Tabbara et al. (1999) *Eur. J. Ophthalomol.* 9:1–7). Recently, nHu-IFN-alpha administered by the oral mucosa route has been shown to stimulate output (Ship et al. (1999) *J. Interferon Cytokine Res.* 19:480–488).

Hence, the present invention provides a method of administering cytokines, particularly, IFN-α and IFN-β, such that the compounds directly enter the nasal lymphatic system. The interferon will then be distributed to the lymphatics of the head and neck region altering the function of the lymphocytes that affect the lacrimal and salivary glands. It is further recognized that delivery of the cytokine via the trigeminal or the olfactory nerve can result in the direct delivery of the cytokine to the lacrimal gland. This direct delivery of the interferon to the lymphatics of the head and neck region or directly to the lacrimal gland will reduce lymphocyte infiltration of the lacrimal and salivary glands and treat Sjogren's Syndrome.

An "effective amount" of a cytokine to treat Sjogren's Syndrome using the administration method of the present invention will be sufficient to reduce or lessen the clinical symptoms of Sjogren's Syndrome. As such, an effective amount of the cytokine leads to an improved clinical status of a patient suffering from Sjogren's Syndrome in comparison to an untreated patient. For instance, an improved clinical status of the oral symptoms of Sjogren's Syndrome includes, for example, an overall increase in mouth wetness, an improvement in the ability to swallow dry food, an improvement in the ability to speak continuously, etc. Further, an effective concentration encompasses any improvement in the ocular manifestations of Sjogren's Syndrome including, for example, increase in the wetness of eyes (i.e., a lessening of the sandy or gritty feeling under the eyelids), an increase in tearing, and a decrease in burning sensations, redness, itching, and eye fatigue. Improvements also encompass an improvement in lacrimal function (i.e., a reduction in lymphocyte infiltration into the lacrimal gland). A more extensive description of the clinical manifestation of Sjogren's Syndrome can be found in *Harrion's Principles of Internal Medicine* (McGraw Hill, 1994), pp. 1662–1664, herein incorporated by reference.

Treatment of Viral Infections

In another embodiment, the present method can be employed to deliver cytokines and/or antiviral agents to the lymphatic system, CNS, brain, and/or spinal cord for the treatment, diagnosis or prevention of disorders or disease resulting from viral infection.

As used herein "treating or preventing viral infection" means to inhibit virus transmission, or to prevent the virus from establishing itself in its host CNS, brain or spinal cord, or to ameliorate or alleviate the symptoms of the disease caused by viral infection. The treatment is considered therapeutic if there is a reduction in viral load in the CNS, brain, or spinal cord, decrease in mortality, and/or morbidity. Of particular interest is the administration of a cytokine (particularly IFN-α or IFN-β) by the methods of the invention for the treatment or prevention of viral hepatitis.

Viral hepatitis refers to an infection of the liver caused by a group of viruses having a particular affinity for the liver and include hepatitis A virus, hepatitis B virus, hepatitis C virus, hepatitis D virus, and hepatitis E virus. Of particular interest is the use of the present invention for the treatment of hepatitis C.

Acute infection with hepatitis C virus results in persistent viral replication and progression to chronic hepatitis in approximately 90% of cases. While chronic hepatitis C infection is commonly treated with IFN-β and IFN-α, less than 50% of the patients have sustained remission following treatment (i.e., the eradication of hepatitis C virus). See, for example, Barbaro et al. (1999) *Scand. J. Gastroenterol.* 9:928–933; Oketani et al. (1999) *J. Clin. Gastroenterol.* 28:49–51; and, Kakizaki et al. (1999) *J. Viral Hepatitis* 6:315–319; all of which are herein incorporated by reference. Similarly, IFN therapy has also been demonstrated to be an effective treatment for chronic hepatitis B, however only 25–40% of the patients profit from a long-term beneficial response to the current interferon therapies. Combination therapies for viral hepatitis have also been developed, which combine IFN-therapy with antiviral agents such as ribavirin. These IFN/antiviral therapies are usually given systemically (i.e., intravenously), and hence, the therapeutic agents are not able to cross the blood-brain barrier. Thus, the hepatitis virus can harbor in the central nervous system where the therapeutic agents cannot penetrate. Re-infection and relapse to viral hepatitis symptoms subsequent to treatment frequently occurs. In addition, viral hepatitis infection of the CNS can have serious neurologic consequences. See, for example, Bolay et al. (1996) *Clin. Neurol. Neurosurg.* 98:305–308, herein incorporated by reference. Therefore, new methods of treatment are necessary in the treatment of viral hepatitis. The methods of the present invention can be used to administer a cytokine and/or an antiviral agent or any combination thereof, to the lymphatic system, CNS, brain and/or spinal cord for the treatment or prevention of viral hepatitis. The methods of the invention can be used in conjunction with the existing treatments for viral hepatitis to aid in reducing the clinical symptoms of hepatitis.

As used herein, an "effective amount" of a cytokine or an antiviral agent for the treatment of viral hepatitis using the administration method of the present invention will be sufficient to reduce or lessen the clinical symptoms of hepatitis. As such, an effective amount of the cytokine or antiviral agent administered by the methods of the present invention will augment the activity of the systemically administered antiviral/immunomodulatory compounds used in the art for the treatment of viral hepatitis. As such, the methods of the invention enhance survival and/or improve clinical status of the treated animals in comparison to animals treated with systemic administration methods alone. Improvement in clinical status includes, for example, the prevention of the progression of acute viral hepatitis to chronicity, the reduction of the viral load in chronic hepatitis, and/or the prevention or reduction in the frequency of re-infection and relapse of viral hepatitis symptoms, and/or prevent or reduce the neurologic damage resulting from the viral infection.

Antiviral agents and cytokines of particular interest include, for example, ribavirin, thymosins, and cytokines, such as, IFN-β, IFN-α, and IFN-γ. See, for example, Musch et al. (1998) *Hepato-Gastroenterology* 45:2282–2294; Barbaro et al (1999) *Scand. J. Gastroenterol* 9(34):928–933; Oketani et al. (1999) *J. Clin. Gastroenterol.* 28:49–51; Kakizaki et al. (1999) *J. Viral Hepatitis* 6:315–319; U.S. Pat. No. 6,030,785; U.S. Pat. No. 5,676,942; and U.S. Pat. No. 6,001,799; all of which are herein incorporated by reference.

The course of the viral hepatitis and its response to the treatments administered by the methods of the present invention may be followed by clinical examination and laboratory findings that are commonly performed in the art. For instance, elevated serum alanine aminotransferase (ALT) and aspartate aminotransferase (AST) are known to occur in uncontrolled hepatitis C. A complete response to treatment is generally defined as the normalization of these serum enzymes, particularly ALT (Davis et al. (1989) *New England J. Med.* 321:1501–6). Alternatively, hepatitis C virus replication in subjects in response to the antiviral/immunomodulatory treatment of the present invention can be followed by measuring hepatitis C virus RNA in serum samples by, for example, a nested polymerase chain reaction assay that uses two sets of primers derived from the NS3 and NS4 non-structural gene regions of the HCV genome (Farci et al. (1991) *New England J. Med.* 325:98–104; Ulrich et al. (1990) *J. Clin. Invest.* 86:1609–14).

In another embodiment, the methods of the present invention can be used to treat or prevent herpes simplex viral infection. Herpes simplex viruses (HSV- 1 and HSV-2) produce a variety of infections involving mucocutaneous surfaces, the central nervous system, and occasionally visceral organs. For instance, acute viral replication at a peripheral site such as the cornea is followed by viral entry into neuronal termini. Corneal infection is followed by intraaxonal transport, which moves the virus to the trigeminal ganglia, where further replication may occur before clearance of infectious virus and the establishment of latency. Failure to clear the virus may result in central nervous system infection, encephalitis, and death. Latency may periodically break down in response to certain stimuli, leading to viral reactivation and shedding. The present invention provides a method of administering a cytokine (via, for example, the trigeminal or olfactory nerve) to the trigeminal ganglia and/or the CNS, thereby allowing for the treatment and/or prevention of herpes simplex viral infection.

The immune response to acute herpes simplex virus infection involves both innate and acquired immunity. Key mediators of innate resistance to viral infection include cytokines, particularly interferons such as IFN-α, IFN-β, and IFN-γ. For instance, IFN-α has been shown to inhibit the onset of immediate-early herpes simplex virus gene expression (Oberman et al. (1988) *J. Gen. Virol.* 69:1167–1177). Furthermore, in mice IFN-α and IFN-β are potent inhibitors of replication in the cornea. Specifically, studies have shown that following corneal inoculation in mice, herpes simplex viral titer in both the eyes and trigeminal ganglia was enhanced by up to 1000 fold in mice mutant for IFN-α or IFN-β compared to wild-type control mice (Leib et al. (1999) *J. Exp. Med.* 189:663–672, herein incorporated by reference). The same study further demonstrated that IFNs significantly reduce productive viral infection and reduce the spread of virus from intact corneas. Related studies have also been preformed by Minagawa et al. (1997) *Antiviral Res.* 36:99–105.

In addition, IFN-α and IFN-β activate host defenses such as natural killer cells, which have themselves been shown to be important in controlling herpes simplex virus infection and pathology (Bouley et al. (1996) *Clin. Immunol. Immunopathol.* 80:23–30). IFN-α and IFN-β have also been suggested to be important for limiting progress of infection from peripheral tissues to the nervous system (Halford et al. (1997) *Virology* 236:328–337). Furthermore, IFN-γ appears to play an important role in the clearance of herpes simplex virus from the cornea and in resistance to encephalitis, possibly by inhibiting apoptosis of neurons (Bouley et al. (1995) *J. Immunol.* 155:3964–3971, Geiger et al. (1997) *Virology* 238:189–197, and Imanishi et al. (2000) *J. Biochem.* 127:525–530). Hence, interferons, particularly IFN-α, IFN-β, and IFN-γ, play a major role in limiting herpes simplex viral replication in the cornea, trigiminal ganglia, and in the nervous system.

An "effective amount" of a cytokine for the treatment of herpes simplex virus using the administration method of the present invention will be sufficient to reduce or lessen the clinical symptoms of herpes simplex virus. As such, an effective amount of the cytokine administered by the methods of the present invention will attenuate the activity of the virus and thereby enhance survival and/or improve clinical status of the treated animal in comparison to the untreated control. Improvement in clinical status includes, for example, the prevention or reduction of encephalitis and/or apoptosis in the central nervous system (i.e, increase in neuroprotection), a decrease in the severity of infection (i.e., enhancing viral clearance from the cornea, the trigeminal ganglia, and the CNS), a decrease in viral spread, an increase in the maintenance of latency, and/or a decrease in the frequency of herpes simplex recurrences. More extensive details regarding the clinical manifestations of herpes simplex that can be improved upon the administration of an effective concentration of a cytokine can be found in *Harrion's Principles of Internal Medicine* (McGraw Hill, 1994), pp. 782–787, herein incorporated by reference.

In another embodiment, the methods of the invention can be used for the treatment of human immunodeficiency virus (HIV). HIV is an infectious disease of the immune system characterized by a progressive deterioration of the immune system in most infected subjects. During disease progression, key cells associated with the immune system become infected with HIV, including, e.g., CD4$^+$ T cells, macrophages/monocytes, and glial cells. Prolonged HIV infection frequently culminates in the development of AIDS. In the late stages of this disease, the immune system is severely compromised due to loss or dysfunction of CD4$^+$T cells (Shearer et al. (1991) *AIDS* 5:245–253). The nervous system is also a major target of HIV infection. The virus is carried to the brain by infected monocytes and the neurologic manifestations of HIV infection are thought to arise from viral products and soluble factors produced by the infected macrophages/microglia. Thus, the HIV virus can harbor in the central nervous system where the therapeutic agents cannot penetrate. Re-infection and relapse to HIV symptoms subsequent to treatment frequently occurs. Accordingly, the present invention provides a method of administering a cytokine, particularly an interferon such as IFN-α, IFN-β, and IFN-γ, to the CNS or the lymphatic system for the treatment or prevention of HIV infection.

Interferons are known to exert pleiotropic antiretroviral activities and affect many different stages of the HIV infectious cycle. For instance, IFN-β influences uptake of HIV particles (Vieillard et al. (1994) *Proc. Natl. Acad. Sci. USA* 91:2689–2693); reverse transcription of viral genomic RNA into proviral DNA (Baca-Regen et al. (1994) *J. Virol.* 68:7559–7565: Kombluth et al. (1990) *Clin. Immunol. Immunopathol.* 54:200–219 and Shirazi et al. (1993) *Virology* 193:303–312); viral protein synthesis (Coccia et al. (1994) *J. Biol. Chem.* 269:23087–23094); and packaging and release of viral particles (Poli et al. (1989) *Science* 244:575–577). In addition, virions released from IFN-β treated cells are up to 1,000-fold less infectious than equal numbers of virions released from untreated cells (Hansen et al. (1992) *J. Virol* 66:7543–7548). Furthermore, recent studies have shown that genetically engineered human CD4$^+$ T cells producing constitutively low amounts of IFN-β can eradicate HIV in vivo using a mouse animal model that supports persistent, replicative HIV infection. These results indicated that a therapeutic strategy based upon IFN-β transduction of CD4$^+$ T cells may be successful in controlling a preexisting HIV infection and allowing immune restoration. See, for example, Vieillard et al. (1999) *J. Virol.* 73:10281–10288, herein incorporated by reference. IFN-γ has also been shown to modulate the susceptibility of macrophages to HIV (Zaitseva et al. (2000) *Blood* 96:3109–3117).

It is recognized that administration of the cytokine via the methods of the present invention for the treatment of HIV can be used in combination with any other HIV treatment or therapy known in the art. Therapies used in the treatment of HIV infection include, for example, anti-retroviral drugs, such as reverse transcriptase inhibitors, viral protease inhibitors, and viral entry inhibitors (Caliendo et al. (1994) *Clin. Infect. Dis.* 18:516–524). More recently, treatment with combinations of these agents, known as highly active antiretroviral therapy (HAART), has been used to effectively suppress replication of HIV (Gulick et al. (1997) *N. Engl. J. Med.* 337:734–9 and Hammer et al. (1997) *N. Engl. J. Med.* 337:725–733).

An "effective amount" of a cytokine for the treatment of HW using the administration method of the present invention will be sufficient to reduce or lessen the clinical symptoms of HIV. As such, an effective amount of the cytokine administered by the methods of the present invention will attenuate the activity of the virus (i.e., have a direct antiviral effect) and/or improve the HIV-induced immunological dysfuntions (i.e., enhance the ability of an HIV-infected patient to effectively mount a cellular immune defense against actively replicating HIV). Regardless of the mechanism of action, an effective amount of a cytokine will enhance survival and/or improve clinical status of the treated animals in comparison to the untreated control. Improvement in clinical status includes, for example, a reduction in preexisting HIV infection and/or the rate of disease progression; enhanced $CD4^+$ T-cell survival; suppression of cytokine dysregulation caused by HIV (i.e., enhanced Th1-like cytokine expression); inhibition of viral replication; and improvement in the proliferative expansion of antigen-selected lymphocytes, more particularly the HIV antigen-specific $CD8^+$ subset of T cells, in response to an increase in viral load. Assays to measure these various improvements are known in the art. See, for example, Vieillard et al. (1999) *J. Virol.* 73:10281–10288, Vieillard et al. (1997) *Proc. Natl. Acad. Sci. USA* 94:11595–11600; U.S. Pat. No. 5,911,990 and U.S. Pat. No. 5,681,831; all of which are herein incorporated by reference. More extensive details regarding the clinical manifestations of HIV that can be improved upon the administration of an effective concentration of a cytokine can be found in *Harrion's Principles of Internal Medicine* (McGraw Hill, 1994), pp. 1559–1617, herein incorporated by reference.

Treatment of Proliferative Disorders of the CNS

In another embodiment, the present method can be employed to deliver cytokines to the lymphatic system, CNS, brain, and/or spinal cord for the treatment, diagnosis or prevention of a proliferation disorder or disease.

Cytokines have anti-proliferative activity. For instance, interferons have been shown to have both a direct cytotoxic effect on tumor cells and an indirect cytotoxic effect through the activation of natural killer cells, macrophages, or other immune cells. Specifically, studies have suggested IFN-γ mediated anti-tumor activity, results from modulating the interplay of B and T cell components of the immune system, as well as the inhibition of tumor angiogenesis (Saleh et al. (2000) Gene Ther 7:1715–24). IFN-α has also been shown to significantly decrease average tumor size and increase the average survival time of the treated mammal (Wang et al. (1999) *J Neuropathol Exp. Neurol.* 58:847–58). Intratumoral injection of liposomes containing the human IFN-β gene in nude mice inhibits tumor growth, with complete tumor regression occurring following multiple Intratumoral injections of the gene. Furthermore, IFN-β has been demonstrated to be an effective treatment of high grade astrocytomas (Natsume et al. (1999) *Gene Ther.* 9:1626–33 and Fine et al. (1997) *Clin. Cancer Res* 3: 381–7). The antiproliferative effect of IFN-β appears to occurs through an arrest in the ordered progression through S phase or decreasing the entry into G2/M phase of the cell cycle (Garrison et al. (1996) *J Neurooncol* 30:213–23). Hence, interferons, particularly IFN-α, IFN-β, and IFN-γ, are effective agents for the treatment or prevention of a proliferation disorder of the CNS, spinal cord, brain and lymphatic system.

By "proliferation disorder" is intended any disorder characterized by cellular division occurring in defiance of the normal tissue homeostasis mechanism. The proliferation disorder can be either malignant or benign and result from either an increase in the rate of cell proliferation or a decrease in the rate of cell death. The proliferative disorder treated by the methods of the invention may be at any stage of development (i.e., an early stage with minimal or microscopic tumor burdens or at advanced stages of tumor development).

Proliferative disorders of the central nervous system, brain, or spinal cord include, for example, gliomas, neuronal tumors, poorly differentiated neoplasms, and meningiomas. Gliomas derived from glial cells include astrocytomas (i.e., fibrillary astrocytomas, glioblastoma multiforme, pilocytic astrocytoma, pleomorphic xanthastrocytoma, and brain stem glioma), oligodendrogliomas, and ependymomas and paraventricular mass lesions (i.e., myxopapillary ependymomas, subependymomas, choroid plexus papillomas). Neural tumors comprise CNS tumors that contain mature-appearing neurons (ganglion cells) that may constitute the entire cell population of the lesion or, alternatively, the lesion is an admixture with a glial neoplasm. Poorly differentiated neoplasms include, for example, medulloblastomas. Other proliferative disorders of the CNS, brain or spinal cord include, primary brain lymphoma, meningiomas, and metastatic tumors.

It is recognized that administration of the cytokine via the methods of the present invention for the treatment of a proliferative disorder can be used in combination with any other treatment or therapy known in the art for the treatment of proliferation disorders. Therapies used in the treatment of proliferative disorders include, for example, any form of radiation and chemotherapy treatments. See, for example, Hatano et al. (2000) *Acta Neurochir* 142:633–8, Burton et al. (1999) *Curr Opin Oncol.* 11:157–61, and Brandes et al. (2000) Anticancer Res 20:1913–20; all of which are herein incorporated by reference.

An "effective amount" of a cytokine for the treatment of a proliferative disease or disorder using the administration method of the present invention will be sufficient to reduce or lessen the morphological and/or clinical symptoms of the proliferative disorder. As such, an effective amount of the cytokine administered by the methods of the present invention will exert any physiological response that decreases proliferation of tumor cells and thereby enhances survival and/or improves clinical status of the treated animal in comparison to the untreated control. Such physiological responses include, for example, activation of immune cells, inhibition of cell proliferation, induction of cell differentiation, up-regulation of class I major histocompatiblity complex antigens, inhibition of angiogenesis, and establishment of the T helper 1 (Th1)-type response. Improvement in clinical status includes, for example, an increase in the survival rate of the treated mammal (i.e., an increase in either the one or two year survival rate) and a decrease in tumor size. Assays to measure these various improvements are known in the art. See, for example, Hong et al. (2000) *Clin. Cancer Res.* 6:3354–60); Knupfer et al (2000) *Cytokine* 12:409–12; Natsume et al. (1999) *Gene Ther* 6:1626–33; and U.S. Pat. No. 4,846,782, all of which are herein incorporated by reference. More extensive details regarding the clinical manifestations of proliferative disorders of the CNS, brain, spinal cord, or lymphatic system that can be improved upon the administration of an effective concentration of a cytokine can be found in *Harrion's Principles of Internal Medicine* (McGraw Hill, 1994), herein incorporated by reference.

The present invention may be better understood with reference to the following examples. These examples are intended to be representative of specific embodiments of the invention, and are not intended as limiting the scope of the invention.

EXPERIMENTAL

Example 1

Intranasal Administration of IFN-β to the CNS

Introduction

Administering interferon-β (IFN-β) intranasally is an effective means for delivering this cytokine to the CNS of an animal.

Materials and Methods

Intranasal Delivery to the CNS

Male Sprague-Dawley rats, 199 and 275 grams, were anesthetized with intraperitoneal pentobarbital (40 mg/kg). Drug delivery to the CNS was assessed after intranasal administration of 51 picomoles and 57 picomoles of $^{125}$I-IFN-β in 20 mM Hepes, pH 7.5, to the light and heavy rat, respectively. Rats were placed on their backs and administered ~100 microliters $^{125}$I-IFN-β to each naris over 10–22 minutes, alternating drops every 2–3 minutes between the left and right nares. During the intranasal administration of IFN-β, one side of the nose and the mouth were held closed. This method of administering the cytokine allows for both pressure and gravity to deliver the agent into the upper one third of the nasal cavity. Rats subsequently underwent perfusion-fixation within minutes following the completion of $^{125}$I-IFN-β administration. Perfusion-fixation was performed with 50–100 ml physiologic saline followed by 500 ml of fixative containing 4% paraformaldehyde in 0.1 M Sorenson's phosphate buffer, pH 7.4, prior to brain and spinal cord dissection and $^{125}$I measurement by gamma counting. Areas dissected included the spinal cord, olfactory bulbs, frontal cortex, anterior olfactory nucleus, hippocampal formation, choroid plexus, diencephalon, medulla, pons, and cerebellum.

Results

Rapid appearance of radiolabel was observed throughout the spinal cord, brain stem, and brain, with the concentrations ranging from about 3 pM to about 93 pM. Detailed results are shown below in Table 1. The observation of substantial concentrations of interferon-β in the olfactory and trigeminal nerves suggests that this cytokine is transported through or along these nerves. Tissues with biologically significant levels of interferon-β include the olfactory bulbs, frontal cortex, caudate putamen, anterior olfactory nerve, hippocampal formation, choroid plexus, diencephalon, pons, medulla, ventral dura, trigeminal nerve, olfactory epithelium, circle of Willis, and upper cervical spinal cord.

TABLE 1

Data for the intranasal (I.N.) delivery of Betaseron to the CNS

| Tissue type | Concentration (pM) (51 picomole dose) | Concentration (pM) (57 picomole dose) |
| --- | --- | --- |
| Left olfactory bulb | 89.5 | 51.4 |
| Right olfactory bulb | 92.9 | 67.7 |
| Frontal cortex | 9.19 | 29.1 |
| Caudate/putamen | 7.09 | 34.0 |
| Anterior olfactory nerve | 46.9 | 97.4 |
| Hippocampal formation (left) | 5.81 | 11.7 |
| Hippocampal form (right) | 11.1 | 21.0 |
| Choroid plexus | 79.0 | 33.2 |
| Diencephalon | 15.5 | 24.0 |
| Midbrain | 10.9 | 19.8 |
| Pons | 16.9 | 49.4 |
| Medulla | 24.7 | 90.2 |
| Cerebellum | 10.2 | 30.4 |
| Dura (ventral) | 263.0 | 896 |
| Trigeminal nerve | 36.7 | 362 |
| Left olfactory epithelium | 3697 | |
| Circle of Willis | | 189 |
| Upper Cervical Spinal Cord | 24.3 | 455 |
| Cervical spinal cord | | 6.88 |
| Thoracic spinal cord | 4.0 | 2.55 |
| Lumbar spinal cord | 2.08 | 3.5 |
| Right olfactory epithelium | 22,540 | |

Further quantitation studies for the intranasal delivery of [$^{125}$I] BETASERON® were performed in Sprague-Dawley rats essentially described above. The results are summarized in Table 2. Scans of coronal brain tissue sections showed prominent labeling of the olfactory bulb, caudate/putamen, septal nucleus, periventricular white matter, optic nerve, and superior colliculus (data not shown). These results are in agreement with the results provided in Table 1. The quantitative studies performed in six animals, following internasal administration of about 6 nmol of BETASERON®, demonstrated consistent delivery to a wide variety of CNS structures. Highest concentrations of IFN-β were found in the olfactory bulbs (9 nM), anterior olfactory nucleus (3.3 nM), midbrain (1.9 nM), medulla (1.8 nM), pons (1.6 nM), and cerebellum (1.4 nM). Moderate concentrations were observed in the hippocampal formation (1.3 nM), diencephalon (1.3 nM), frontal cortex (1.1 nM), cervical spinal cord (1.1 nM), and caudate/putamen (0.83 nM).

The very high concentrations of [$^{125}$I] BETASERON® observed in the trigeminal nerve (14 nM) and ventral dura mater (19 nM) strongly suggest that delivery to the CNS involves movement not only along the olfactory neural pathway but also along the trigeminal nerve pathway. Trigeminal delivery should result in high levels in both the olfactory areas and midbrain and brain stem regions. Delivery to the spinal cord probably occurs via the trigeminal pathway. Consistent with trigeminal delivery, [$^{125}$I] BETASERON® reaches the spinal cord within 25 minutes, and exhibits decreasing concentration as you move down the spinal cord.

These results indicate the direct transport of IFN-β along one or more neural pathways into the CNS, brain, and spinal cord.

TABLE 2

Concentration (nM) IFN-β (Betaseron) in Different Rat Tissues Following I.N. Administration of $^{125}$I-IFN-β + IFN-β.

| Tissue | IF11 | IF12 | IF13 | IF14 | IF15 | IF16 | Mean | SE |
|---|---|---|---|---|---|---|---|---|
| Blood Sample 1 | 1.12 | 1.53 | 0.92 | 0.74 | 1.70 | 0.85 | 1.1 | 0.2 |
| Blood Sample 2 | 2.77 | 3.26 | 1.44 | 2.11 | 3.13 | 2.74 | 2.6 | 0.3 |
| Blood Sample 3 | 3.72 | 6.62 | 2.81 | 3.87 | 5.02 | 4.22 | 4.4 | 0.5 |
| Blood Sample 4 | 5.37 | 6.35 | 7.38 | 5.4 | 7.32 | 5.50 | 6.2 | 0.4 |
| Blood Sample 5 | 7.29 | | | 6.69 | 8.15 | 7.95 | 7.5 | 0.3 |
| Left Olfactory Bulb | 9.02 | 6.11 | 3.01 | 5.93 | 18.29 | 18.46 | 10 | 3 |
| Right Olfactory Bulb | 5.6 | 6.99 | 3.39 | 4.84 | 15.26 | 12.48 | 8.1 | 1.9 |
| Frontal Cortex | 1.12 | 1.24 | 1.09 | 0.44 | 1.72 | 1.19 | 1.1 | 0.2 |
| Caudate/Putamen | 0.68 | 0.91 | 0.83 | 0.36 | 1.08 | 1.11 | 0.83 | 0.11 |
| Ant. Olf. Nucleus | 2.11 | 2.55 | 1.96 | 1.09 | 6.82 | 5.50 | 3.3 | 0.9 |
| L. Hippocampal Form. | 0.84 | 1.63 | 1.24 | 0.37 | 2.23 | 1.71 | 1.3 | 0.3 |
| R. Hippocampal Form. | 0.85 | 1.77 | 1.24 | 0.40 | 1.84 | 1.91 | 1.3 | 0.3 |
| Diencephalon | 0.86 | 1.52 | 1.39 | 0.44 | 2.05 | 1.72 | 1.3 | 0.2 |
| Midbrain | 0.80 | 1.69 | 1.53 | 0.44 | 5.07 | 1.91 | 1.9 | 0.7 |
| Pons | 0.76 | 1.91 | 1.76 | 0.38 | 2.71 | 2.04 | 1.6 | 0.4 |
| Medulla | 0.63 | 2.41 | 2.90 | 0.42 | 2.29 | 2.08 | 1.8 | 0.4 |
| Cerebellum | 0.89 | 1.72 | 1.56 | 0.36 | 2.19 | 1.84 | 1.4 | 0.3 |
| Ventral Dura | 2.47 | 46.16 | 10.89 | 7.13 | 21.35 | 23.52 | 19 | 6 |
| Trigeminal Nerve | 7.94 | 12.14 | 19.89 | 4.57 | 24.44 | 17.63 | 14 | 3 |
| Spinal Dura | | | 0.59 | 0.13 | | 0.29 | 0.34 | 0.13 |
| Cervical Spinal Cord | 0.33 | 0.88 | 3.12 | 0.38 | 0.98 | 1.00 | 1.1 | 0.4 |
| Thoracic Spinal Cord | 0.14 | 0.11 | 0.39 | 0.29 | 0.33 | 0.15 | 0.24 | 0.05 |
| Lumbar Spinal Cord | 0.13 | 0.12 | 0.27 | 0.22 | 0.32 | 0.10 | 0.19 | 0.04 |
| Deltoid Muscle | 0.62 | 0.58 | 0.50 | 1.10 | 0.67 | 0.22 | 0.62 | 0.12 |
| Liver | 0.58 | 0.78 | 1.01 | 1.38 | 0.54 | 0.31 | 0.77 | 0.16 |
| Kidney | 0.67 | 0.73 | 2.08 | 5.26 | 0.56 | 1.81 | 1.9 | 0.7 |
| Lung | 1.87 | 0.56 | 2.18 | 0.72 | 0.85 | 0.99 | 1.2 | 0.3 |
| Esophagus | 1.10 | 1.50 | 68.2 | 5234.83 | 1.44 | 22.40 | 888 | 869 |
| Trachea | 1.48 | 3.11 | 83.46 | 4.67 | 1.45 | 5.91 | 17 | 13 |
| L. Olfact. Epithelium | 1175.9 | 75.64 | 14.08 | 1431.14 | 454.41 | 227.29 | 563 | 244 |
| R. Olfact. Epithelium | 2083.1 | 411.32 | 45.66 | 1113.87 | 191.13 | 2765.47 | 1102 | 453 |

IF11–16 represent individual rats
Average weight (g.) across rats: 243 g. (range = 203 g – 268 g)
Average concentration administered: 6.0 n moles (range = 4.8 nmol – 6.9 nmol)
Average radioactivity (uCi): 39 uCi (range = uCi – 52 uCi)

Example 2

Intranasal Administration of IFN-D Retains Pharmacological Activity in the CNS

Assays were performed to determine if IFN-β, delivered intranasally, retained pharmacological activity in the CNS. IFN-β activates signal transduction pathways via a cell surface IFN receptor. The IFN receptor is part of a prototypical JAK-STAT signaling complex. It has two transmembrane chains that associate with intracellular signaling proteins including TYK2, JAK1, and two latent transcription factors termed "signal transducers and activators of transcription" (STATs). Binding of IFN-β to the receptor brings the two Janus kinases (TYK2 and JAK1) near each other, and they become activated by phosphorylation. The kinases then activate the cytoplasmic tails of the IFN receptors by phosphorylating tyrosine residues. These phosphotyrosines provide docking sites for the STATs, bringing them into appropriate positions for phosphorylation by the nearby Janus kinases. Upon phosphorylation STATs translocate to the nucleus, bind specific DNA elements and direct transcription. Hence, the pharmacological activity of IFN-β following intranasal delivery can be effectively assayed by monitoring the phosphorylation states of TYK2 and STAT1 throughout the brain cortex.

Methods

Control/Drug Treatment

Harlan Sprague-Dawley rats were anesthetized with pentabarbitol (50 mg/kg). 80 µl of either water or IFN-β was intranasally administered in 5 doses over a 20 minute time period. Specifically, 8 µl was administered in 5 doses at 2 minute intervals for each nostril. Recombinant rat interferon-β (rrIFN-β) (35 picomoles) was intranasally administered to rat IF35 (drug-treated) and H$_2$O (vehicle used to dilute rrIFN-β) was administered to rat IF33 (control-treated). After administration the animal was perfused with 100 ml of saline and fixed with 200 ml of 10% formalin. The brain was then removed and sliced in a brain matrix into 2 mm sections. The slices were collected in cassettes and paraffin embedded. Tissue was sliced to 4 µm and placed on microscope slides.

Immunohistological Staining

The antibodies to the phosphorylated forms of proteins TYK2 and STAT1 were purchased from Cell Signaling Technology (product numbers 9321L and 9171S, respectively).

The method of immunohistological staining was as follows. Tissue sections were deparaffinized and hydrated by placing the slides in the following solutions for the indicated times: Xylene for 10 min; 100% EtOH for 5 min; 95% EtOH for 5 min; 70% EtOH for 5 min; and, 50% EtOH for 5 min.

The slides were removed from Coplin jars and washed in H₂O for 2 min on a rocking platform. The antigen (TYK2 and/or STAT1) was unmasked by incubating slides in citrate buffer (pH 6.0) and heating in a vegetable steamer for 45 min. The slides were removed and washed in cold running tap H₂O for 10 min. Slices were incubated in 3% H₂O for 10 min at room temperature (RT) in a humid chamber and subsequently washed in H₂O for 5 min. Next, slides were washed in a tris buffered saline solution (50 mM tris, 150 mm NaCl) with 0.2% Triton X-100 (TBST) for three 5 min washes. Following the wash, the slides were blocked with 2% goat serum in TBST (GSTBST) for 1 hr at RT. Following three 5 min washes in TBST, the slides were incubated with primary antibody (rabbit anti-TYK2 polycolonal antibody; diluted in GSTBST 1:250) in a humid chamber at RT for 30 min and incubated overnight at 4° C. The next day, the slides were wash in TBST for three 5 min washes and incubated with goat anti-rabbit secondary antibody. The secondary antibody was diluted 1:400 in 10 mM phosphate buffered solution (PBS; 137 mM sodium chloride, 2.7 mM potassium chloride) at RT for 1 hr. For the last 15 min of this incubation, the ABC reagent was made (5 ml PBS, 2 drops of reagent A, mix, 2 drops of reagent B, mix; Vector Technology product #PK-6101) and allowed to stand at RT. Slides underwent an additional three 5 minute washes in TBST, followed by incubation with ABC reagent at RT for 1 hr in a humid chamber. An additional three 5 minute washes in TBST followed. Approximately 100–150 µl, enough to cover the tissue, of diaminobenzidine tetrahydrochloride (DAB) was added and allowed to incubate at RT for 10 min. The reaction was stopped by a 2 minute wash with H₂O. Slides were subsequently washed in H₂O until the solution was clear. Slides were dehydrated in the following solutions for the indicated times: 50% EtOH for 2 min; 70% EtOH for 2 min; 95% EtOH for 2 min; 100% EtOH for 2 min; 50/50 Xylene/ROH for 2 min; and Xylene for 5 min. Excess xylene was removed and slides were mounted by adding 2–3 drops of Vectamount and covered with coverslip. The Vectamount was allowed to dry before viewing.

Results

Induction of the IFN-α/β pathway is characterized by the phosphorylation of TYK2 and STAT1. Therefore, antibodies specific to the phosphorylated forms of TYK2 and STAT1 were used to measure the level of the activated from of these proteins prior to and following intranasal delivery of IFN-β. Quantitation revealed that the levels of phosphorylated TYK2 increased throughout the brain cortex following intranasal delivery of 35 pmol of recombinant rat IFN-β (data not shown). These results demonstrate that IFN-β retains pharmacological activity in the CNS following the intranasal delivery methods of the present invention.

Example 3

Intranasal Administration of IFN-D to the Lymphatic System

Intranasal delivery of [¹²⁵I] BETASERON® was performed in Sprague-Dawley Rats as essentially described in Example 1. 3.9–7.9 nmol BETASERON® was administered in a 44–96 µl volume over the course of 20–29 minutes. Animals were perfused at 30 minutes. Data obtained from eight individual animals is provided in Table 3. Experimental means from this set of experiments are provided in Table 4. These quantitative studies demonstrated delivery of [¹²⁵I] BETASERON® to the superficial cervical nodes and to the deep cervical nodes of the lymphatic system. On average, 6.1 nM BETASERON® was found in the superficial cervical nodes, and 31.5 nM was found in the deep cervical nodes following the administration methods of the invention. These results are summarized in Table 5.

TABLE 3

Betaseron Concentration (nM) Following I.N. Administration of ¹²⁵I-IFNβ + rhIFNβ

| Experiment | IF34 | IF36 | IF37 | IF38 |
|---|---|---|---|---|
| MicroCi | 31 | 47 | 61 | 48 |
| Nmol | 3.9 | 6.9 | 7.9 | 6.6 |
| Blood Sample #1 | 0.53 | 0.58 | 1.1 | 1.6 |
| Blood Sample #2 | 1.6 | 4.3 | 2.8 | 3.9 |
| Blood Sample #3 | 2.4 | 3.1 | 4.6 | 6.2 |
| Blood Sample #4 | 3.6 | 4.7 | 5.1 | 8.3 |
| Blood Sample #5 | 4.1 | 7.0 | 7.0 | 10 |
| Blood Sample #6 | | 8.2 | 8.5 | 10 |
| Left Olfactory Epithelium | 65 | 862 | 388 | 643 |
| Right Olfactory Epithelium | 62 | 1103 | 1447 | 1876 |
| Left Olfactory Bulb | 1.6 | | 3.5 | 5.6 |
| Right Olfactory Bulb | 1.3 | | 8.1 | 7.1 |
| Anterior Olfactory Nucleus | 0.96 | | 1.3 | 2.5 |
| Frontal Cortex | 0.28 | | 0.84 | 0.97 |
| Caudate/Putamen | 0.09 | | 0.57 | 1.7 |
| L + R Hippocampus | 0.38 | | 0.62 | 0.82 |
| Left Hippocampus | | | | |
| Right Hippocampus | | | | |
| Diencephalon | 0.65 | | 0.74 | 0.95 |
| Midbrain | 0.48 | | 0.61 | 0.88 |
| Pons | 0.45 | | 0.75 | 0.91 |
| Medulla | 0.36 | | 0.76 | 0.95 |
| Cerebellum | 0.34 | | 0.54 | 0.69 |
| Ventral Brain Dura | 6.1 | 9.7 | 12 | 14 |
| Optic Nerve + Chiasm | 1.2 | 6.3 | 4.4 | 25 |
| Trigeminal Nerve | 5.8 | 12 | 8.5 | 20 |
| Spinal Dura | 0.09 | 0.16 | 0.67 | 1.1 |
| Upper Cervical Cord | 0.43 | 2.3 | 0.92 | 1.1 |
| Cervical Spinal Cord | 0.17 | 0.21 | 0.47 | 1.3 |
| Thoracic Spinal Cord | 0.13 | 0.20 | 0.35 | 0.58 |
| Lumbar Spinal Cord | 0.17 | 0.29 | 0.39 | 0.49 |
| Superficial Cervical Nodes | 8.1 | 6.3 | 4.0 | 6.1 |
| L. Superficial Cervical Node | 3.9 | | | |
| R. Superficial Cervical Node | 4.2 | | | |
| Deep Cervical Nodes | 9.7 | 16 | | 68 |
| Left Deep Cervical Node | | | | |
| Right Deep Cervical Node | | | | |
| Common Carotids | 14 | 27 | 38 | 22 |
| Thyroid | 250 | 462 | 830 | 725 |
| Esophagus | 145 | 196 | 394 | 715 |
| Trachea | 177 | 41863 | 692 | 553 |
| Muscle | 0.52 | 0.64 | 0.74 | 1.1 |
| Liver | 0.47 | 1.9 | 0.83 | 1.2 |
| Kidney | 1.0 | 0.79 | 2.92 | 1.8 |
| Lung | 0.66 | 1.7 | 2.4 | 27 |

TABLE 4

Experimental Means of Betaseron Concentrations (nM) following I.N. Administration of ¹²⁵I-IFNβ + rhIFNβ

| | Avg for IF34, 37, 38 microCi/nmol | |
|---|---|---|
| | 46.67 Mean | 6.13 Std Dev |
| Blood Sample #1 | 1.1 | 0.53 |
| Blood Sample #2 | 2.7 | 1.2 |
| Blood Sample #3 | 4.4 | 1.9 |
| Blood Sample #4 | 5.7 | 2.4 |
| Blood Sample #5 | 7.1 | 3.1 |
| Blood Sample #6 | 9.5 | 1.4 |
| Left Olfactory Epithelium | 365 | 290 |
| Right Olfactory Epithelium | 1128 | 948 |

TABLE 4-continued

Experimental Means of Betaseron Concentrations (nM) following I.N. Administration of $^{125}$I-IFNβ + rhIFNβ

| | Avg for IF34, 37, 38 microCi/nmol | |
|---|---|---|
| | 46.67 Mean | 6.13 Std Dev |
| Left Olfactory Bulb | 3.6 | 2.0 |
| Right Olfactory Bulb | 5.5 | 3.7 |
| Anterior Olfactory Nucleus | 1.6 | 0.81 |
| Frontal Cortex | 0.70 | 0.37 |
| Caudate/Putamen | 0.80 | 0.85 |
| L + R Hippocampus | 0.61 | 0.22 |
| Left Hippocampus | | |
| Right Hippocampus | | |
| Diencephalon | 0.78 | 0.16 |
| Midbrain | 0.66 | 0.20 |
| Pons | 0.71 | 0.24 |
| Medulla | 0.69 | 0.30 |
| Cerebellum | 0.52 | 0.17 |
| Ventral Brain Dura | 11 | 4.3 |
| Optic Nerve + Chiasm | 10 | 13 |
| Trigeminal Nerve | 11 | 7.5 |
| Spinal Dura | 0.61 | 0.49 |
| Upper Cervical Cord | 0.83 | 0.36 |
| Cervical Spinal Cord | 0.65 | 0.59 |
| Thoracic Spinal Cord | 0.35 | 0.23 |
| Lumbar Spinal Cord | 0.35 | 0.17 |
| Superficial Nodes | 6.0 | 2.1 |
| Left Superficial Cervical Node | | |
| Right Superficial Cervical Node | | |
| Deep Cervical Nodes | 39 | 41 |
| Left Deep Cervical Node | | |
| Right Deep Cervical Node | | |
| Common Carotids | 25 | 12 |
| Thyroid | 602 | 309 |
| Esophagus | 418 | 286 |
| Trachea | 474 | 266 |
| Muscle | 0.78 | 0.27 |
| Liver | 0.82 | 0.35 |
| Kidney | 1.9 | 0.95 |
| Lung | 10 | 15 |

TABLE 5

Summary of Betaseron Concentration (nM) in the Cervical Lymph Nodes Following I.N. Administration $^{125}$1-IFNβ + rhIFNβ

| Experiment | IF34 | IF36 | IF37 | IF38 | Average | Std Dev |
|---|---|---|---|---|---|---|
| MicroCi | 31 | 47 | 61 | 48 | | |
| Nmol | 3.9 | 6.9 | 7.9 | 6.6 | | |
| Superficial Cervical Nodes | 8.1 | 6.3 | 4.0 | 6.1 | 6.1 | 1.7 |
| Deep Cervical Nodes | 9.7 | 16 | | 68 | 31 | 32 |

Average Dose Administered = 46.75 uCi and 6.32 nmol

Example 4

Intravenous Administration of BETASERON®

Intravenous administration of BETASERON® was studied in order to determine the extent to which delivery to the CNS and/or lymphatic system following intranasal administration may be due to absorption from the nasal cavity into the circulation, followed by subsequent delivery to the CNS and lymphatics.

Male Harlan Sprague-Dawley rats weighing 263–318 g were used for these experiments. Rats were anaesthetized with sodium pentobarbital (Nembutal, 50 mg/kg). For each rat, a 500 μl solution containing $^{125}$I-IFN-β and rhIFN-β in 0.9% NaCl was delivered intravenously over 60–90 seconds through a cannula into the femoral vein. On average, 560 pmol and 49 μCi of IFN-β were administered to each rat. Then 0.2 ml of blood was collected from the descending aorta cannula every 5 minutes for a total of five blood samples. Lastly, the rat was perfused through the descending aorta cannula with 60–90 ml of 0.9% NaCl followed by 400 ml of fixative (4% paraformaldehyde in Sorenson's phosphate buffer). Individual tissue sections were dissected out, placed in 5 ml Startedt tubes, and then counted for gamma rays in the Packard Cobra II autogamma counter.

The methods described above created the same general blood level of BETASERON® with intravenous delivery as that achieved in the intranasal administration studies. Tables 6 and 7 provide the level of BETASERON® in the blood following either intravenous injection and intranasal administration. The level of BETASERON® in the blood following intravenous administration and intranasal administration over time is shown graphically in FIG. 1.

This study demonstrated that very little of the intravenously administered BETASERON® reaches either the CNS or lymphatics. Consequently, it is clear that the intranasal method of delivery described in this application is very beneficial in targeting the CNS and lymphatics of the head and neck region. This method of delivery does not utilize the circulation to reach the CNS or lymphatics, but rather bypasses the circulation and blood-brain barrier to accomplish delivery. Because it is not necessary to use the circulatory system to deliver the medication to the CNS and/or lymphatics, systemic side effects can be significantly reduced.

TABLE 6

Level of Betaseron in the blood following intravenous administration.

| Experiment # | IF47 | IF49 | IF50 | Mean | Std Err |
|---|---|---|---|---|---|
| Delivered nmol | 0.521 | 0.579 | 0.579 | 0.560 | 0.019 |
| Delivered uCi | 56 | 46 | 45 | 49 | 4 |
| 5 min Blood Sample | 6.30 | 4.47 | 6.78 | 5.85 | 0.70 |
| 10 min Blood Sample | 5.35 | 4.41 | 5.29 | 5.01 | 0.30 |
| 15 min Blood Sample | 5.90 | 4.14 | 5.95 | 5.33 | 0.60 |
| 20 min Blood Sample | 5.95 | 4.48 | 5.92 | 5.45 | 0.49 |
| 25 min Blood Sample | 6.40 | 4.16 | 6.30 | 5.62 | 0.73 |

TABLE 7

Level of Betaseron in the blood stream following intranasal administration.

| Experiment # | IF36 | IF37 | IF38 | IF40 | Mean | Std Err |
|---|---|---|---|---|---|---|
| Delivered nmol | 6.890 | 7.947 | 6.583 | 7.360 | 7.195 | 0.30 |
| Delivered uCi | 47 | 61 | 48 | 51 | 52 | 3 |
| 5 min Blood Sample | 0.58 | 1.08 | 1.60 | 2.44 | 1.43 | 0.40 |
| 10 min Blood Sample | 1.43 | 2.76 | 3.89 | 5.91 | 3.50 | 0.95 |
| 15 min Blood Sample | 3.06 | 4.62 | 6.22 | 8.30 | 5.55 | 1.12 |
| 20 min Blood Sample | 4.70 | 5.14 | 8.27 | 10.17 | 7.07 | 1.30 |
| 25 mm Blood Sample | 6.93 | 7.04 | 10.16 | 12.85 | 9.25 | 1.42 |

TABLE 8

Concentration (nM) following intravenous administration of IFN-β.

| | IF47 | IF49 | IF50 | Mean | Std Err |
|---|---|---|---|---|---|
| Delivered nmol | 0.521 | 0.579 | 0.579 | 0.560 | 0.019 |
| Delivered uCi | 56 | 46 | 45 | 49 | 4 |
| Blood Sample#1 (5 min) | 6.30 | 4.47 | 6.78 | 5.85 | 0.70 |

TABLE 8-continued

Concentration (nM) following intravenous administration of IFN-β.

|  | IF47 | IF49 | IF50 | Mean | Std Err |
|---|---|---|---|---|---|
| Blood Sample#2 (10 min) | 5.35 | 4.41 | 5.29 | 5.02 | 0.30 |
| Blood Sample#3 (15 min) | 5.90 | 4.14 | 5.95 | 5.33 | 0.60 |
| Blood Sample#4 (20 min) | 5.95 | 4.47 | 5.92 | 5.45 | 0.49 |
| Blood Sample#5 (25 min) | 6.40 | 4.16 | 6.30 | 5.62 | 0.73 |
| Left Olfactory Epithelium | 0.27 | 0.72 | 0.86 | 0.62 | 0.18 |
| Right Olfactory Epithelium | 0.19 | 0.78 | 1.04 | 0.67 | 0.25 |
| Left Olfactory Bulb | 0.63 | 0.23 | 0.31 | 0.39 | 0.12 |
| Right Olfactory Bulb | 1.01 | 0.22 | 0.23 | 0.49 | 0.26 |
| Anterior Olfactory Nucleus | 0.15 | 0.13 | 0.17 | 0.15 | 0.01 |
| Frontal Cortex | 0.15 | 0.16 | 0.18 | 0.16 | 0.01 |
| Caudate/Putamen | 0.21 | 0.11 | 0.15 | 0.16 | 0.03 |
| Hippocampus | 0.13 | 0.11 | 0.14 | 0.13 | 0.01 |
| Cerebellum | 0.15 | 0.12 | 0.16 | 0.14 | 0.01 |
| Diencephalon | 0.14 | 0.12 | 0.14 | 0.13 | 0.01 |
| Midbrain | 0.16 | 0.12 | 0.14 | 0.14 | 0.01 |
| Pons | 0.13 | 0.11 | 0.03 | 0.09 | 0.03 |
| Medulla | 0.14 | 0.11 | 0.14 | 0.13 | 0.01 |
| Dorsal Brain Dura |  | 0.41 | 0.43 | 0.42 | 0.01 |
| Ventral Brain Dura | 1.32 | 0.28 | 0.17 | 0.59 | 0.37 |
| Optic Nerve + Chiasm |  | 0.18 | 0.29 | 0.24 | 0.04 |
| Trigeminal Nerve | 0.28 | 0.21 | 0.26 | 0.25 | 0.02 |
| Spinal Dura | 0.07 | 0.13 | 0.12 | 0.11 | 0.02 |
| Upper Cervical Cord | 0.15 | 0.12 | 0.09 | 0.12 | 0.02 |
| Cervical Cord | 0.10 | 0.10 | 0.09 | 0.10 | 0.00 |
| Thoracic Spinal Cord | 0.08 | 0.09 | 0.11 | 0.09 | 0.01 |
| Lumbar Spinal Cord | 0.11 | 0.12 | 0.14 | 0.12 | 0.01 |
| Superficial Nodes | 0.42 | 0.28 | 0.64 | 0.45 | 0.10 |
| Deep Cervical Nodes | 0.10 | 0.34 | 0.40 | 0.28 | 0.09 |
| Axial Nodes |  | 0.33 | 0.64 | 0.49 | 0.13 |
| Common Carotids | 0.13 | 0.11 | 0.09 | 0.11 | 0.01 |
| Thyroid | 52.65 | 56.49 | 11.03 | 40.06 | 14.56 |
| Esophagus | 0.92 | 0.91 | 0.29 | 0.71 | 0.21 |
| Trachea | 0.81 | 0.49 | 0.46 | 0.59 | 0.11 |
| Deltoid Muscle | 0.29 | 0.19 | 0.30 | 0.26 | 0.04 |
| Liver | 15.17 | 11.82 | 16.90 | 14.63 | 1.49 |
| Kidney | 1.30 | 1.51 | 1.49 | 1.43 | 0.07 |
| Lung | 16.02 | 30.02 | 33.14 | 26.39 | 5.26 |

It should be noted that, as used in this specification and the appended claims, the singular forms "a," "an," and "the" include plural referents unless the content clearly dictates otherwise. Thus, for example, reference to a composition containing "a compound" includes a mixture of two or more compounds.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

That which is claimed:

1. A method for administering a human interferon-β (IFN-β) or a biologically active variant thereof to the central nervous system or the lymphatic system of a mammal, said mammal in need of said IFN-β to reduce or treat an infection or disorder by producing a therapeutic effect on the central nervous system or the lymphatic system, comprising:
   administering a pharmaceutical composition comprising IFN-β or a variant thereof to a tissue of a nasal cavity of the mammal wherein a therapeutically effective amount of the IFN-β or the variant thereof is transported via an olfactory neural pathway to the central nervous system or the lymphatic system of the mammal, wherein the IFN-β or variant thereof provides the therapeutic effect on the central nervous system or the lymphatic system, wherein said biologically active variant has at least 70% sequence identity to the human interferon-β and retains antiviral activity or anti-proliferative activity, and wherein said infection or disorder is selected from viral meningitis, herpes simplex, hepatitis-C, HIV, multiple sclerosis, and a glioma.

2. The method of claim 1, wherein the transported IFN-β or variant thereof provides the therapeutic effect on the central nervous system.

3. The method of claim 2, wherein the tissue of the nasal cavity is the roof of the nasal cavity.

4. The method of claim 2, wherein the tissue of the nasal cavity is an olfactory area of the nasal cavity.

5. The method of claim 2, wherein the transported IFN-β or the variant thereof reduces a viral infection selected from viral meningitis, herpes simplex, hepatitis-C, and human immunodeficiency (HIV).

6. The method of claim 2, wherein the transported IFN-β or variant thereof treats multiple sclerosis.

7. The method of claim 2, wherein the transported IFN-β or the variant thereof treats a glioma.

8. The method of claim 2, wherein the IFN-β or the variant thereof is administered in a dosage range from about 0.14 nmol/kg of brain weight to about 138 nmol/kg of brain weight.

9. The method of claim 2, wherein the tissue of the nasal cavity is in the upper one third of the nasal cavity.

10. The method of claim 2, wherein the IFN-β or the variant thereof is transported to a cerebellum, a superior colliculus, a periventricular white matter, an optic nerve, a midbrain, a pons, a olfactory bulb, an anterior olfactory nucleus, or any combination thereof.

11. The method of claim 2, wherein the IFN-β or the variant thereof is transported to spinal cord, a brain stem, a cortical structure, a subcortical structure, or any combination thereof.

12. The method of claim 2, wherein said human IFN-β is the mature human IFN-β.

13. The method of claim 12, wherein the biologically active variant thereof has the amino acid sequence of mature IFN-β with a serine substitution for the cysteine residue at position 17.

14. The method of claim 1, wherein the transported IFN-β or the variant thereof provides the therapeutic effect on the lymphatic system.

15. The method of claim 14, wherein the tissue of the nasal cavity is in the upper one third of the nasal cavity.

16. The method of claim 14, wherein the tissue of the nasal cavity is the roof of the nasal cavity.

17. The method of claim 14, wherein the tissue of to nasal cavity is an olfactory area of the nasal cavity.

18. The method of claim 14, wherein the IFN-β or the variant thereof is transported to a deep cervical node, a superficial cervical node, or any combination thereof.

19. The method of claim 14, wherein the IFN-β or the variant thereof is administered in a dosage range of about 0.14 nmol/kg of brain weight to about 138 nmol/kg of brain weight.

20. The method of claim 14, wherein said human IFN-β is the mature human IFN-β.

21. The method of claim 20, wherein the biologically active variant thereof has the amino acid sequence of mature IFN-β with a serine substitution for the cysteine residue at position 17.

22. The method of claim 14, wherein the transported IFN-β or the variant thereof reduces a viral infection selected from viral meningitis, herpes simplex, hepatitis-C, and human immunodeficiency (HIV).

23. The method of claim 14, wherein the transported IFN-β or the variant thereof treats multiple sclerosis.

24. The method of claim 14, wherein the transported IFN-β or the variant thereof treats a glioma.

25. The method of claim 14, wherein the IFN-β or the variant thereof is administered in a dosage range from about 0.02 pmol/kg of brain weight to about 138 nmol/kg of brain weight.

26. The method of claim 1, wherein the pharmaceutical composition further comprises an odorant.

27. The method of claim 26, wherein the odorant is lipophillic.

28. The method of claim 26, wherein the odorant stimulates odorant-sensitive enzymes and/or modifies ion channels within the olfactory system to enhance absorption of the IFN-β or the variant thereof.

29. The method of claim 26, wherein the odorant is selected from a terpanoid, an aldehyde, an ester, and a jasmine.

30. The method of claim 29, wherein the odorant is selected from cetralva, citronellol, a cinnamaldehyde, octyl isovalerate, C1S-jasmine, jasmal and musk 89.

31. The method of claim 26, wherein the odorant binds to or has high affinity for an OBP to facilitate passage through the mucosa to the olfactory receptors.

32. A method for administering a human interferon-β IFN-β or a biologically active variant thereof to the central nervous system or the lymphatic system of a mammal, said mammal in need of said IFN-β to reduce or treat an infection or disorder by producing a therapeutic effect on the central nervous system or the lymphatic system, comprising:
    administering a pharmaceutical composition comprising IFN-β or a variant thereof and an odorant to a tissue of a nasal cavity of the mammal, wherein a therapeutically effective amount of the IFN-β or the variant thereof is transported to the central nervous system or the lymphatic system of the mammal, wherein the IFN-β or variant thereof provides the therapeutic effect on the central nervous system or the lymphatic system, wherein said biologically active variant has at least 70% sequence identity to the human interferon-β—and retains antiviral activity or anti-proliferative activity, and wherein said infection or disorder is selected from viral meningitis, herpes simplex, hepatitis-C, HIV, multiple sclerosis, and a glioma.

33. The method of claim 32, wherein the odorant is lipophillic.

34. The method of claim 32, wherein the odorant binds to or has high affinity for an OBP to facilitate passage through the mucosa to the olfactory receptors.

35. The method of claim 32, wherein the tissue of the nasal cavity is an olfactory area of the nasal cavity.

36. The method of claim 32, wherein the transported IFN-β or variant thereof provides the therapeutic effect on the central nervous system.

37. The method of claim 32, wherein the transported IFN-β or the variant thereof provides the therapeutic effect on the lymphatic system.

38. The method of claim 32, wherein the biologically active variant thereof has the amino acid sequence of mature IFN-β with a serine substitution for the cysteine residue at position 17.

39. A method for administering a human interferon-β (IFN-β) or a biologically active variant thereof to the central nervous system or the lymphatic system of a mammal, said mammal in need of said IFN-β to reduce or treat an infection or disorder by producing a therapeutic effect on the central nervous system or the lymphatic system, comprising:
    administering a pharmaceutical composition comprising IFN-β or a variant thereof to a tissue in a nasal cavity of the mammal, wherein a therapeutically effective amount of the IFN-β or the variant thereof is administered to the upper one third of the nasal cavity and is transported to the central nervous system or the lymphatic system of the mammal, wherein the IFN-β or variant thereof provides the therapeutic effect on the central nervous system or the lymphatic system, wherein said biologically active variant has at least 70% sequence identity to the human interferon-β and retains antiviral activity or anti-proliferative activity, and wherein said infection or disorder is selected from viral meningitis, herpes simplex, hepatitis-C, HIV, multiple sclerosis, and a glioma.

40. The method of claim 39, wherein the transported IFN-β or variant thereof provides the therapeutic effect on the central nervous system.

41. The method of claim 40, wherein the IFN-β or the variant thereof is transported to a cerebellum, a superior colliculus, a periventricular white matter, an optic nerve, a midbrain, a pons, an olfactory bulb, an anterior olfactory nucleus, or any combination thereof.

42. The method of claim 39, wherein the transported IFN-β or the variant thereof provides the therapeutic effect on the lymphatic system.

43. The method of claim 42, wherein the IFN-β or to variant thereof is transported to a deep cervical node, a superficial cervical node, or any combination thereof.

44. The method of claim 39, wherein the biologically active variant thereof has the amino acid sequence of mature IFN-β with a serine substitution for to cysteine residue at position 17.

45. The method of claim 39, wherein said human IFN-β is the mature human IFN-β.

46. The method of claim 39, wherein the tissue of the nasal cavity is the roof of the nasal cavity.

47. The method of claim 39, wherein the pharmaceutical composition further comprises an odorant.

48. The method of claim 39, wherein the IFN-β or the variant thereof is administered in a dosage range from about 0.02 pmol/kg of brain weight to about 138 nmol/kg of brain weight.

* * * * *